(12) United States Patent
Shih et al.

(10) Patent No.: US 8,549,933 B2
(45) Date of Patent: Oct. 8, 2013

(54) ALL ELECTRIC PIEZOELECTRIC FINGER SENSOR (PEFS) FOR SOFT MATERIAL STIFFNESS MEASUREMENT

(75) Inventors: Wan Y. Shih, Bryn Mawr, PA (US); Wei-Heng Shih, Bryn Mawr, PA (US); Anna Markidou, Souni-Limassol (CY); Steven T. Szweczyk, Springfield, PA (US); Hakki Yegingil, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 169 days.

(21) Appl. No.: 13/268,225

(22) Filed: Oct. 7, 2011

(65) Prior Publication Data

US 2012/0053489 A1    Mar. 1, 2012

Related U.S. Application Data

(63) Continuation of application No. 12/837,590, filed on Jul. 16, 2010, now Pat. No. 8,033,185, which is a continuation of application No. 12/328,639, filed on Dec. 4, 2008, now Pat. No. 7,779,707, which is a continuation of application No. 11/136,173, filed on May 24, 2005, now Pat. No. 7,497,133.

(60) Provisional application No. 60/573,869, filed on May 24, 2004.

(51) Int. Cl.
*G01L 1/04*    (2006.01)

(52) U.S. Cl.
USPC .................................................. 73/862.639

(58) Field of Classification Search
USPC ............................................ 73/862.639, 105
See application file for complete search history.

(56) References Cited

U.S. PATENT DOCUMENTS

| | | | |
|---|---|---|---|
| 3,205,464 | A | 9/1965 | Schwartz |
| 4,093,883 | A | 6/1978 | Yamamoto |
| 4,302,694 | A | 11/1981 | Fujishima et al. |
| 4,349,762 | A | 9/1982 | Kitamura et al. |
| 4,363,993 | A | 12/1982 | Nishigaki et al. |

(Continued)

FOREIGN PATENT DOCUMENTS

| | | |
|---|---|---|
| EP | 0631319 A1 | 12/1994 |
| EP | 1536227 A2 | 6/2005 |

(Continued)

OTHER PUBLICATIONS

Wellman, P. S. et al., "Tactile Imaging: A Method for Documenting Breast Lumps".

(Continued)

*Primary Examiner* — Lisa Caputo
*Assistant Examiner* — Octavia D. Hollington
(74) *Attorney, Agent, or Firm* — Mendelsohn, Drucker & Dunleavy, P.C.

(57) ABSTRACT

A PEFS (Piezoelectric Finger Sensor) acts as an "electronic finger" capable of accurately and non-destructively measuring both the Young's compression modulus and shear modulus of tissues with gentle touches to the surface. The PEFS measures both the Young's compression modulus and shear modulus variations in tissue generating a less than one-millimeter spatial resolution up to a depth of several centimeters. This offers great potential for in-vivo early detection of diseases. A portable hand-held device is also disclosed. The PEF offers superior sensitivity.

18 Claims, 22 Drawing Sheets

(56) References Cited

U.S. PATENT DOCUMENTS

| | | | |
|---|---|---|---|
| 4,403,166 A * | 9/1983 | Tanaka et al. ............... 310/332 | |
| 4,528,502 A | 7/1985 | Rocha | |
| 4,649,312 A | 3/1987 | Robin et al. | |
| 4,802,371 A | 2/1989 | Calderara et al. | |
| RE33,691 E * | 9/1991 | Harnden et al. ............. 310/332 | |
| 5,054,323 A | 10/1991 | Hubbard et al. | |
| 5,313,535 A | 5/1994 | Williams | |
| 5,334,835 A | 8/1994 | Nakayama et al. | |
| 5,338,999 A | 8/1994 | Ramakrishnan et al. | |
| 5,382,864 A | 1/1995 | Morikawa et al. | |
| 5,445,008 A | 8/1995 | Wachter et al. | |
| 5,475,318 A | 12/1995 | Marcus et al. | |
| 5,503,010 A | 4/1996 | Yamanaka | |
| 5,553,486 A | 9/1996 | Bonin | |
| 5,626,728 A | 5/1997 | Ramakrishnan et al. | |
| 5,689,063 A | 11/1997 | Fujiu et al. | |
| 5,719,324 A | 2/1998 | Thundat et al. | |
| 5,780,727 A | 7/1998 | Gimzewski et al. | |
| 5,807,758 A | 9/1998 | Lee et al. | |
| 5,866,807 A | 2/1999 | Elings et al. | |
| 5,874,126 A | 2/1999 | Kahn et al. | |
| 5,948,993 A | 9/1999 | Ting et al. | |
| 5,966,787 A | 10/1999 | Nakayama et al. | |
| 5,996,412 A | 12/1999 | Hansen | |
| 6,075,585 A | 6/2000 | Minne et al. | |
| 6,278,379 B1 | 8/2001 | Allen et al. | |
| 6,280,396 B1 | 8/2001 | Clark | |
| 6,289,717 B1 | 9/2001 | Thundat et al. | |
| 6,336,366 B1 | 1/2002 | Thundat et al. | |
| 6,422,069 B1 | 7/2002 | Shimizu et al. | |
| 6,458,327 B1 | 10/2002 | Vossmeyer et al. | |
| 6,465,368 B2 | 10/2002 | Inoue et al. | |
| 6,589,727 B1 | 7/2003 | Klenerman et al. | |
| 6,621,080 B2 | 9/2003 | Yamamoto | |
| 6,734,425 B2 | 5/2004 | Hantschel et al. | |
| 6,781,285 B1 | 8/2004 | Lazarus et al. | |
| 6,903,491 B2 | 6/2005 | Irie et al. | |
| 6,992,421 B2 | 1/2006 | Ikeda et al. | |
| 7,022,540 B2 * | 4/2006 | Kim et al. ..................... 438/50 | |
| 7,055,378 B2 | 6/2006 | Su et al. | |
| 7,083,270 B2 | 8/2006 | Torii et al. | |
| 7,084,554 B2 | 8/2006 | Xu et al. | |
| 7,088,378 B1 | 8/2006 | Su et al. | |
| 7,104,134 B2 | 9/2006 | Amano et al. | |
| 7,195,909 B2 | 3/2007 | Klenerman et al. | |
| 7,263,874 B2 | 9/2007 | Fitch et al. | |
| 7,458,265 B2 | 12/2008 | Shih et al. | |
| 7,497,133 B2 | 3/2009 | Shih et al. | |
| 7,521,257 B2 * | 4/2009 | Adams et al. ................ 436/183 | |
| 7,744,773 B2 | 6/2010 | Shih et al. | |
| 7,942,056 B2 | 5/2011 | Mutharasan et al. | |
| 7,992,431 B2 | 8/2011 | Shih et al. | |
| 2002/0094528 A1 | 7/2002 | Salafsky | |
| 2002/0117659 A1 | 8/2002 | Lieber et al. | |
| 2002/0155303 A1 | 10/2002 | Wielstra et al. | |
| 2003/0032293 A1 | 2/2003 | Kim et al. | |
| 2003/0068655 A1 | 4/2003 | Bottomley et al. | |
| 2003/0194697 A1 | 10/2003 | Klenerman et al. | |
| 2003/0224551 A1 | 12/2003 | Kim et al. | |
| 2003/0235681 A1 | 12/2003 | Sebastian et al. | |
| 2004/0022677 A1 | 2/2004 | Wohlstadter et al. | |
| 2004/0265664 A1 | 12/2004 | Badding et al. | |
| 2005/0112621 A1 | 5/2005 | Kim et al. | |
| 2005/0114045 A1 | 5/2005 | Giurgiutiu et al. | |
| 2005/0199047 A1 | 9/2005 | Adams et al. | |
| 2005/0277852 A1 | 12/2005 | Shih et al. | |
| 2005/0287680 A1 | 12/2005 | Venkatasubbarao et al. | |
| 2006/0053870 A1 | 3/2006 | Berndt | |
| 2006/0217893 A1 | 9/2006 | Li et al. | |
| 2006/0223691 A1 | 10/2006 | Shih et al. | |
| 2006/0228657 A1 | 10/2006 | Masters et al. | |
| 2006/0257286 A1 | 11/2006 | Adams | |
| 2007/0089515 A1 | 4/2007 | Shih et al. | |
| 2007/0141721 A1 | 6/2007 | Vafai et al. | |
| 2007/0169553 A1 | 7/2007 | Mutharasan | |
| 2007/0218534 A1 | 9/2007 | Klenerman et al. | |
| 2008/0034840 A1 | 2/2008 | Mutharasan | |
| 2008/0035180 A1 | 2/2008 | Mutharasan | |
| 2009/0007645 A1 | 1/2009 | Shih et al. | |
| 2009/0053709 A1 | 2/2009 | Mutharasan | |
| 2009/0078023 A1 | 3/2009 | Mutharasan | |
| 2009/0203000 A1 | 8/2009 | Mutharasan | |
| 2010/0068697 A1 | 3/2010 | Shih et al. | |
| 2010/0239463 A1 | 9/2010 | Shih et al. | |

FOREIGN PATENT DOCUMENTS

| | | |
|---|---|---|
| WO | 98/50773 A2 | 11/1998 |
| WO | 2004/061991 A1 | 7/2004 |
| WO | 2005/043126 A2 | 5/2005 |
| WO | 2006/031072 A1 | 3/2006 |
| WO | 2007/087328 A2 | 8/2007 |
| WO | 2007/133619 A1 | 11/2007 |
| WO | 2008/020903 A2 | 2/2008 |
| WO | 2008/021187 A2 | 2/2008 |
| WO | 2008/021189 A2 | 2/2008 |
| WO | 2008/101199 A1 | 8/2008 |
| WO | 2009/014830 A1 | 1/2009 |
| WO | 2009/035732 A2 | 3/2009 |
| WO | 2009/035732 A3 | 3/2009 |

OTHER PUBLICATIONS

Weng, L. et al., "Effect of acetylacetone on the preparation of PZT materials in sol/gel processing", Mater, Sci. Engin., B96: 307-312 (2002).

Wilson, L S et al., "Elastography—the movement begins", Phys. Med. Biol., 45: 1409-1421 (2000).

Wilson, L., et al., "Pezoelectric-excited millimeter-sized cantilever (PEMC) sensor provides viscosity and density measurements," Submitted to Review of Scientific Instruments, 1-26.

Yi, J. W. et al., "Effect of length, width, and mode on the mass detection sensitivity of piezoelectric unimorph cantilevers", J. Appl. Phys., 91(3): 1680-1686 (2002).

Yi, J. W. et al., "In situ cell detection using piezoelectric lead zirconate titanate-stainless steel cantilevers", J. Appl. Phys., 93(1): 619-625 (2003).

Zhao, Q. et al., "Array adsorbent-coated lead zirconate titanate (PZT)/stainless steel cantilevers for dimethyl methylphosphonate (DMMP) detection", Sensors and Actuators, B117(1): 74-79 (2006). Abstract Only.

Zhou, J. et al., "Zeolite-modified microcantilever gas sensor for indoor air quality control," Sensors and Actuators B, Oct. 1, 2003, 94(3), 337-342.

Zhu, D.M. et al., "Thermal conductivity and electromechanical property of single-crystal lead magnesium niobate titanate", Appl. Phys. Lett., 75(24): 3868-3870 (1999).

Data of Commercially Available Product, EDO Corporation: 1-8 (1999).

Data of Commercially Available Product, APC International, Ltd.: 1-2 (2005).

Campbell, G.A., et al., "Use of Piezoelectric-Excited millimeter Sized Cantilever Sensors to Measure Albumin Interaction with Self-Assembled Monolayers of Alkanethiols Having Different Functional Headgroups," Anal. Chem. 78, 2328-2334 (2006).

Campbell, G.A., et al., "Method of measuring *Bacillus anthracis* spores in the Presence of copious amounts of *Bacillus thurigiensis* and *Bacillus cereus*," Anal. Chem. 79, 1145-1152 (2007).

Campbell, G.A., et al., "PEMC sensor's mass change sensitivity is 20 pg/Hz under liquid immersion," Biosensors and Bioelectronics, 22, 35-41 (2006).

Campbell, G.A., et al., "Detection of *Bacillus anthracis* spores and a model protein usings PEMC sensors in a flow cell at 1 mL/min," Biosensors and Bioelectronics, 22, 78-85 (2006).

Campbell, G.A., et al., "Detection of airborne *Bacillus anthracis* spores by an integrated system of an air sampler and a cantilever immunosensor," Sensors and Actuators B 127, 376-382 (2007).

Maraldo, et al., "Method for Label-Free Detection of Femtogram Quantities of Biologics in Flowing Liquid Samples," Anal. Chem. 79, 2762-2770 (2007).

(56) References Cited

OTHER PUBLICATIONS

Maraldo, et al., "Detection and confirmation of staphylococcal enterotoxin B in apple juice and milk using piezoelectric-excited millimeter-sized cantilever sensors at 2.5 fg/mL," Anal Chem. 79, 7636-7643 (2007).
Maraldo, et al., "Method for Quantification of a Prostate Cancer Biomarker in Urine without Sample Preparation," Anal. Chem. 79, 7683-7690 (2007).
Maraldo, et al., "10-Minute assay for detecting *Escherichia coli* O157:H7 in ground beef samples using piezoelectric-excited millimeter-size cantilever sensors." Journal of Food Protection, vol. 70, No. 7, 1670-1677 (2007).
Maraldo, et al., "Preapration-Free Method for Detecting *Escherichia coli* O157:H7 in the Presence of Spinach, Spring Lettuce Mix, and Ground Beef Particulates," Journal of Food Protection, vol. 70, No. 11, 2651-2655 (2007).
Rijal, et al., "PEMC-based method of measuring DNA hybridization at femtomolar concentration directly in human serum and in the presence of copious noncomplementary strands," Anal. Chem., 79, 7392-7400 (2007).
Rijal, et al., "Method for measuring the Self-Assembly of Alkanethiols on Gold at Femtomolar Concentrations," Langmuir, 23, 6856-6863 (2007).
Wilson, et al., "Viscosity and density values from excitation level response of piezoelectric-excited cantilever sensors," Sensors and Actuators A 138, 44-51 (2007).
Gu, et al., "Single-Calcination Synthesis of Pyrochlore-Free 0.9Pb (Mg1/3Nb2/3)03-0.1PbTiO3 and Pb(Mg1/3Nb2/3) O3 Ceramics using a Coating Method," J. Am. Ceram. Soc., 86 [2] 217-21 (2003).
Thaysen, et al., "Cantilever-Based Bio-Chemical Sensor Integrated in a Microliquid Handling System," 401-404 (2001).
Li, et al., Micromachined Biomimetic Sensor Using a Modular Artificial Hair Cells, pp. 1-3.
Thaysen, "Label free Detection, BioMEMs Materials and Fabrication Methods," Track 2, 3:00pm, pp. 1-3, Sep. 7, 2002.
Habib Ammaru, Ohin Kwon, Jim Keun Seo, and Eung Je Woo, T-Scan Electrical Impedance Imaging System for Anomaly Detection, Siam J., Appl. Math., vol. 65, No. 1, pp. 252-266 © 2004 Society for Industrial and Applied Mathematics.
Amanuma, K. et al., "Crystallization behavior of sol-gel derived Pb(Zr,Ti)O3 thin films and the polarization switching effect on film microstructure", Appl. Phys. Lett., 65(24): 3140-3142 (1994).
Ammari, H. et al., "T-Scan Electrical Impedance Imaging System for Anomaly Detection", Siam J. Appl. Math., 65(1): 252-266 (2004).
Baselt, D. R. et al., "Biosensor based on force microscope technology", J. Vac. Sci. Technol. B, 14(2): 789-793 (1996).
Birnie, III, D. P. et al., "Coating uniformity and device applicability of spin coated sol-gel PXT films", Microelectronic Engineering, 29: 189-192 (1995).
Bondoux, C. et al., "MgO insulating films prepared by sol-gel route for SiC substrate", J. Europe. Ceramic Soc., 25: 2795-2798 (2005).
Brito, R. et al., "Adsorption of 3-mercaptopropyltrirnethoxysilane and 3-aminopropylthoxysilane at platinum electrodes", J. Electroanalytical Chem., 520: 47-52 (2002).
Campbell, G.A., et al., "Piezoelectric excited millimeter-sized cantilever (PEMC) sensor detects *Escherichia coli* O157:H7 in two-hour incubated samples at 4 CFU per gram of beef," J. of Rapid Methods and Automation in Mirobiology, 1-39.
Campbell, G.A., et al., "Detection and quantification of proteins using self-excited PZT-glass millimeter-sized cantilever," Biosensors and Bioelectronics, 26-36.
Campbell, G.A., "Piezoelectric-excited millimeter-sized cantilever (PEMC) sensors detect *Bacillus anthracis* at 300 spores/mL," Biosensors and Bioelectronics, 37-45.
Campbell, G.A., et al., "kinetics of *Bacillus anthracis* spore binding to antibody functionalized PEMC sensors in presence of *Bacillus thuringiensis* and *Bacillus cereus*," J. Publications, Am. Chem. Soc. 25 pages.
Campbell, G.A., et al., "*Escherichia coli* O157:H7 detection limit of millimeter-sized PZT cantilever sensors in 700 cells/mL," Analytical Sci., 11-13.
Campbell, G.A., et al, "Detection of pathogen *Escherichia coli* O157:H7 using self-excited PZT-glass microcantilevers," Biosensors and Boelectronics, 14-25.
Campbell, G.A., "Detection of staphylococcus enterotoxin B at pictogram levels using piezoelectric-excited millimeter-sized cantilever sensors," Submitted on line to J. of Analytical Chem., 1-24.
Campbell, G.A., et al., "Detect *Escherichia coli* O157:H7 in ground beef samples using piezoelectric excited millimeter-sized cantilever (PEMC) sensors," Submitted on-line to Biosensors and Bioelectronics, 2-34.
Campbell, G.A., et al., "A method for measuring *Escherichia coli* O157:H7 at 1 cell/mL in 1 liter sample using antibody functional piezoelectric-excited millimeter sized cantilever sensor," Paper submitted on-line to J. of Analytical Chemistry. 1-23.
Capobianco, J. A., et al, "Methyltrimethoxysilane- insulated piezoelectric microcantilevers for direct, all-electrical biodetection in buffered aqueous solutions", Rev. Sci. Instrum., 77: 125105-1-125105-6 (2006).
Capobianco, J. A., et al., "3-mercaptopropyltrimethoxysilane as insulating coating and surface for protein immobilization for piezoelectric microcantilever sensors", Rev. Sci. Instrum., 78: 046106-1-046106-3 (2007).
Carlier, S. G., et al., "Elastography", J. Cardiovasc Risk, 9(5): 237-245 (2002).
Carr, D.W., et al., "Fabrication of nanoelectromechanical systems in single crystal silicon using silicon on insulator substrates and electron beam lithography," J. Vac. Sci. Technology, B, 5(6), 2760-2763.
Che, G. et al., "Molecular recognition based on (3-mercaptopropyl) trimethoxysilane modified gold electrodes", J. Electroanalytical Chem., 417: 155-161 (1996).
Chen, G. Y. et al., "Adsorption-induced surface stress and its effects on resonance frequency of microcantilevers", J. Appl. Phys., 77(8): 3618-3622 (1995).
Chen, X. et al., "Electrochemical and Spectroscopic Characterization of Surface Sol-Gel Processes", Langmuir, 20 (20): 8762-8767 (2004).
Cho, S. H. et al., "Micro-scale metallization on flexible polyimide substrate by Cu electroplating using SU-8 photoresist mask", Thin Solid Films, 475: 68-71 (2005).
Duval, F.F.C. et al., "Stable TiO2/Pt electrode structure for lead containing ferroelectric thick films on silicon Mems structures", Thin Solid Films, 444: 235-240 (2003).
Feili, D. et al., "Encapsulation of organic field effect transistors for flexible biomedical microimplants", Sensors and Actuators, A120: 101-109 (2005).
Ferrini, R. et al., "Screening Mammography for Breast Cancer: American College of Preventive Medicine Practice Policy Statement", www.acpm.org/breast, pp. 1-4 (2005).
Fritz, J. et al., "Translating Biomolecular Recognition into Nanomechanics", Science, 288: 316-318 (2000).
Fung, Y. S. et al., "Self-Assembled Monolayers as the Coating in a Quartz Piezoelectric Crystal Immunosensor to Detect Salmonella in Aqueous Solution", Anal. Chem., 73: 5302-5309 (2001).
Gao, L. et al., "Imaging of the elastic properties of tissue: A review", Ultrasound in Med. & Biol., 22(8): 959-977 (1996). Abstract Only.
Greenleaf, J. F. et al., "Selected Methods for Imaging Elastic Properties of Biological Tissues", Annu. Rev. Biomed. Eng., 5: 57-78 (2003).
Gu, H. et al., "Single-Calcination Synthesis of Pyrochlore-Free 0.9Pb(Mg1/3Nb2/3)O3-0.1PbTiO3 and Pb (Mg1/3Nb2/3)O3 Ceramics using a Coating Method", J. Am. Ceram. Soc., 86(2): 217-221 (2003).
Haccart, T. et al., "Evaluation of niobium effects on the longitudinal piezoelectric coeffecients of Pb(Zr,Ti)O3 thin films", Appl. Phys. Lett., 76(22): 3292-3294 (2000).
Han, W. et al, "A magnetically driven oscillating probe microscope for operations in liquids", Appl. Phys. Lett., 69(26): 4111-4113 (1996).

(56) References Cited

OTHER PUBLICATIONS

Hiboux, S. et al., "Mixed titania-lead oxide seed layers for PZT growth on Pt(111): a study on nucleation, texture and properties", J. Europe. Ceram. Soc., 24: 1593-1596 (2004).

Hwang, I.H. et al., "Self-actuating biosensor using a piezoelectric cantilever and its optimization", Journal of Physics: Conference Series 34, pp. 362-367, 2006.

Hwang, K.S. et al., "In-situ quantitative analysis of a prostate-specific antigen (PSA) using a nanomechanical PZT cantilever", Lab Chip, 4: 547-552 (2004).

Ilic, B. et al., "Mechanical resonant immunospecific biological detector", Appl. Phys. Lett., 77(3): 450-452 (2000).

Itoh, T. et al., "Self-excited force-sensing microcantilevers with piezoelectric thin films for dynamic scanning force microscopy", Sensor and Actuators, A54:477-481 (1996).

Jung, S.K. et al., "Polymeric Mercaptosilane-Modified Platinum Electrodes for Elimination of Interferants in Glucose Biosensors", Anal. Chem., 68: 591-596 (1996).

Kanda, T. et al., "A flat type touch probe sensor using PZT thin film vibrator", Sensors and Actuators, 83: 67-75 (2000).

Katiyar, P. et al. "Electrical properties of amorphous aluminum oxide thin films", Acta Materialia, 53: 2617-2622 (2005).

Keller, a. et al., "Reliability of Computed Tomography Measurements of Paraspinal Muscle Cross-Sectional Area and Density in Patients With Chronic Low Back Pain", Spine, 28(13): 1455-1460 (2003).

Kelly, J. et al., "Effect of Composition on the Electromechanical Properties of (1-x)Pb(Mg1/3Nb213)O3-xPbTIO3 Ceramics" J. Am. Ceram. Soc., 80(4): 957-964 (1997).

Khabari, A. et al., "Partially ionized beam deposition of parylene" J. Non-Crystalline Solids, 351: 3536-3541 (2005).

Kim, S.H. et al., "Influence of Al2O3 diffusion barrier and PbTiO3 seed layer on microstructurel and ferroelectric charachteristics of PZT thin films by sol-gel spin coating method," Thin Solid Films, 305: 321-326 (1997).

Kim, S.J. et al., "Fabrication and Characterization of Pb(Zr,Ti)O3 Microcantilever for Resonance Sensors," Jpn. J. Appl. Phys., 42(3): 1475-1478 (2003).

Klissurska, R.D. et al. "Microstructure of PZT sol-gel films on Pt substrates with different adhesion layers," Microelectronic Engineering, 29: 297-300 (1995).

Kruse, S.A. et al., "Tissue characterization using magnetic resonance elastography: preliminary results," Phys. Med. Biol., 45: 1579-1590 (2000).

Kumar, V. et al, "A Simple System for the Preparation of Submicrometer Lead Titanate Powders by the Sol-Gel Method," J. Am. Ceram. Soc., 79(10): 2775-2778 (1996).

Kwok, CLK. et al., "Low temperature perovskite formation of lead zirconate titanate thin films by a seeding process," J. Mater. Res 8(2): 339-344 (1993).

Lee, C. et al., "Sol-gel derived PZT force sensor for scanning force microscopy", Mater. Chem. Phys., 44: 25-29 (1996).

Lee, C. et al, "Self-excited piezoelectric PZT microcantilevers for dynamic SFM—with inherent sensing and actuating capabilities", Sensors and Actuators, A72: 179-188 (1999).

Lee, J. H. et al., "Label free novel electrical detection using micromachined PZT monolithic thin film cantilever for the detection of C-reactive protein", Biosensors and Bioelectronics, 20: 269-275 (2004).

Lee, J. H. et al., "Effect of mass and stress on resonant frequency shift of functionalized Pb(Zr0.52Ti0.48)O3 thin film microcantilever for the detection of C-reactive protein", Appl. Phys. Lett., 84(16): 3187-3189 (2004).

Lee, J. H. et al., "Immunnoassay of prostate-specific antigen (PSA) using resonant frequency shift of piezoelectric nanomechanical microcantilever", Biosensors and Bioelectronics, 20: 2157-2162 (2005).

Lee, S. S. at al., "Self-Excited Piezoelectric Cantilever Oscillators", The 8th International Conference on Solid-State Sensors and Actuators, and Eurosensors IX, Stockholm, Sweden: 417-420 (1995).

Lee, Y. at al., "A Piezoelectric Micro-Cantilever Bio-Sensor Using the Mass-Microbalancing Technique With Self-Excitation", The 13th International Conference on Solid-State Sensors, Actuators, and Microsystems, Seoul, Korea: 644-647 (2005).

Li, S. et al., "The intrinsic nature of nonlinear behavior observed in lead zirconate titanate ferroelectric ceramic", J. Appl. Phys., 69(10): 7219-7224 (1991).

Li, X. et al., "Detection of water-ice transition using a lead zirconate titanate/brass transducer", J. Appl. Phys., 92(1): 106-111 (2002).

Lin, Z. et al "Operation of an Ultrasensitive 30-MHz Quartz Crystal Microbalance in Liquids", Anal. Chem., 65(11): 1546-1551 (1993).

Liu, W. et al., "Preparation and orientation control of Pb1.1(Zr0.3Ti0.7)O3 thin films by a modified sol-gel process", Mat. Lett., 46: 239-243 (2000).

Luo, H. et al., "Synthesis of PMN and 65PMN-35PT Ceramics and Films by a New Suspension Method", Perovskite, Piezoelectric, and Dielectric Ceramics: 251-260.

Luo, H. et al., "Comparison in the Coating of Mg(OH)2 on Micron-Sized and Nanometer-Sized Nb2O5 Particles", Int. J. Appl. Ceram. Technol., 1(2): 146-154 (2004).

Luo, H., "Colloidal Processing of PMN-PT Thick Films for Piezoelectric Sensor Applications", A Thesis Submitted to the Faculty of Drexel University in Jun. 2005.

Maki, K. et al., "Evaluation of Pb(Kr,Ti)O3 Films Derived from Propylene-Glycol-Based Sol-Gel Solutions", Jpn. J. Appl. Phys., 39(9B): 5421-5425 (2000).

Maraldo, D. et al., "Resonant-mode millimeter sized cantilever biosensor for continuous detection of proteins and pathogens in flowing liquids," Dept. of Chem. and Biological Eng., 1-21.

Matsui, Y. et al., "Highly Oxidation-Resistant TiN Barrier Layers for Ferroelectric Capacitors", Jpn. J. Appl. Phys., 36 (3B): 1586-1588 (1997).

Mazza, E. et al., Biomechanics, http://www.zfm.ethz.ch/e/res/bio/, 1-10.

Mcgovern, J.P. et al., "Real-Time Salmonella Detection Using Lead Zirconate Titanate-Titanium Microcantilevers", Mater. Res. Soc. Symp. Proc., 845: AA3.8.1-AA3.8.6 (2005).

Mueller, V. et al, "Nonlinearity and scaling behavior in donor-doped lead zirconate titanate piezoceramic", Appl. Phys. Lett., 72(21): 2692-2694 (1998).

Mulvihill, M. L. et al., "The Role of Processing Variables in the Flux Growth of Lead Zinc Niobate-Lead Titanate Relaxor Ferroelectric Single Crystals", Jpn. J. Appl. Phys., 35(7): 3984-3990 (1996).

Niedziolka, J. et al., "Charaterisation of gold electrodes modified with methyltrimethoxysilane and (3-mercaptopropyl)trimethoxysilane sol-gel processed films", J. Electroanalytical Chem., 578: 239-245 (2005).

Nguyen, L. T. T. et al., "Synthesis and characterization of a photosensitive polyimide precursor and its photocuring behavior for lithography applications", Optical Materials, 29: 610-618 (2007).

Oden, P. I. et al., "Viscous drag measurements utilizing microfabricated cantilevers", Appl. Phys. Lett., 68(26): 3814-3816 (1996).

Ohnmacht, M. et al., "Microcoils and microrelays—An optimized multilayer fabrication process", Sensors and Actuators, 83: 124-129 (2000).

Park, G.T. et al, "Measurement of piezoelectric coefficients of lead zirconate titanate thin films by strain-monitoring pneumatic loading method", Appl. Phys. Lett., 80(24): 4606-4608 (2002).

Park, S.E. et al., "Ultrahigh strain and piezoelectric behavior in relaxor based ferroelectric single crystals", J. Appl. Phys., 82(4): 1804-1811 (1997).

Piezo Systems, Inc., "Piezoceraminc Sheets and Their Properties", Piezo Systems, Inc. Catalog: 1-3 (2007).

Pons, T. et al., "Solution-phase single quantum dot fluorescence resonance energy transfer", J. Amer. Chem. Soc., 128(47): 15324-15331 (2006). Abstract Only.

Ren, W. et al., "Non linear strain and DC bias induced piezoelectric behaviour of electrostrictive lead magnesium niobate-lead titanate ceramics under high electric fields", J. Phys. D: Appl. Phys., 35: 1550-1554 (2002).

(56) References Cited

OTHER PUBLICATIONS

Ren, W. et al., "Nonlinear behavior of piezoelectric lead zinc niobate-lead titanate single crystals under ac electric fields and dc bias", Appl. Phys. Lett., 83(25): 5268-5270 (2003).
Rosenberg, RD et al., "Effects of age, breast density, ethnicity and estrogen replacement therapy on screening mammographic sensitivity and cancer stage at diagnosis: review of 183,134 screening mammograms in Albuquerque, New Mexico", Radiology, 209(2): 511-5118 (1998). Abstract Only.
Saito, Y. et al., "Lead-free piezoceramics", Nature, 432: 84-87 (2004).
Schemmel, A. et al., "Single molecule force spectrometer with magnetic force control and inductive detection", Rev. Sci. Instrum., 70(2): 1313-1317 (1999).
Shen, Z. et al., "Microfabrication of Miniaturized PZT/SiO2 Piezoelectric Microcantilever for Rapid, Direct, In-situ Biosensing", MRS Fall Meeting, Boston: 1-23 (2005).
Shen, Z. et al., "Self-exciting, self-sensing PbZr0.53Ti0.47O3/SiO2 piezoelectric microcantilevers with femtogram/Hertz sensitivity", Appl. Phys. Lett., 89: 023506-1-023506-3 (2006).
Shin, W. et al "Simultaneous liquid viscosity and density determination with piezoelectric unimorph cantilevers", J. Appl. Phys., 89(2): 1497-1505 (2001).
Shih, W. et al., "Ultrasensitive Pathogen Quantification in Drinking Water Using Highly Piezoelectric Microcantilevers", Amer. Chem. Soc., Chapter 23, 179-185 (2005).
Shih, W. et al., "Nanosensors for Environmental Applications", Nanotechnologies for the Life Sciences, 5: 271-293 (2005).
Straub, V. et al., "Contrast Agent-Enhanced Magnetic Resonance Imaging of Skeletal Muscle Damage in Animal Models of Muscular Dystrophy", Magn. Reson. Med., 44: 655-659 (2000).
Thompson, W. R. et al., "Hydrolysis and Condensation of Self-Assembled Monolayers of (3-Mercaptopropyl) trimethoxysilane on Ag and Au Surfaces", Langmuir, 13: 2291-2302 (1997).
Thundat, T. et al., "Detection of mercury vapor using resonating microcantilevers", Appl, Phys. Left., 66(13): 1695-1697 (1995).
Tslonsky, M. et al., "Sol-Gel-Derived Ceramic-Carbon Composite Electrodes: Introduction and Scope of Applications", Anal. Chem., 66: 1747-1753 (1994).
Tu, Y. L. et al., "A study of the effects of process variables on the properties of PZT films produced by a single-layer sol-gel technique", J. Mater. Sci., 30: 2507-2516 (1995).
Udayakumar, K. R. et al., "Thickness-dependent electrical characteristics of lead zirconate titanate thin films", J. Appl. Phys., 77(8): 3981-3986 (1995).
Wang, Q.M. et al., "Nonlinear piezoelectric behavior of ceramic bending mode actuators under strong electric fields", J. Appl. Phys., 86(6): 3352-3360 (1999).
Wang, Y. et al., "Tactile Mapping of Palpable Abnormalities for Breast Cancer Diagnosis".
Ward, M. D. et al., "In Situ Interfacial Mass Detection with Piezoelectric Transducers", Science, 249: 1000-1007 (1990).
Wellman, P. S. et al., "Breast Tissue Stiffness in Compression is Correlated to Histological Diagnosis", http://biorobotics.harvard.edu/pubs/mechprops: 1-15.
Wellman, P. S. et al, "Tactile Imaging of Breast Masses", Arch. Surg., 136: 204-208 (2001).

\* cited by examiner

US 8,549,933 B2

ALL ELECTRIC PIEZOELECTRIC FINGER SENSOR (PEFS) FOR SOFT MATERIAL STIFFNESS MEASUREMENT

This application is a continuation of U.S. patent application Ser. No. 12/837,590, filed on Jul. 16, 2010, currently pending, which, in turn, is a continuation of U.S. patent application Ser. No. 12/328,639, filed on Dec. 4, 2008, now U.S. Pat. No. 7,779,707 issued on Aug. 24, 2010, which, in turn, is a continuation of U.S. patent application Ser. No. 11/136,173, filed on May, 24, 2005, now U.S. Pat. No. 7,497,133, which, in turn, is a non-provisional of U.S. Provisional Application No. 60/573,869, filed May 24, 2004, the entire disclosures of which are hereby incorporated by reference as if set forth fully herein.

STATEMENT OF GOVERNMENT INTEREST

This invention was reduced to practice with Government support under Grant No. R01 EB00720-01 awarded by NIH; the Government is therefore entitled to certain rights to this invention.

BACKGROUND OF THE INVENTION

1. Field of Invention

The present invention relates to a piezoelectric sensor for measuring shear and compression.

2. Brief Description of the Prior Art

A typical soft-material/tissue mechanical property tester requires an external force (displacement) applicator and an external displacement (force) gauge.[1,2] The external force (displacement) generator may be hydraulic or piezoelectric and the external displacement gauge (force gauge) may be optical or piezoelectric. Regardless of the mechanism of force/displacement generation and displacement/force detection, typical tissue/soft-material mechanical testing is destructive and it requires specimens cut to a disc shape to fit in the tester. In addition, a compressive elastic modulus tester e.g., an Instron is also different from a shear modulus tester, e.g., a rheometer.[3] Currently, no single instrument measures both the compressive Young's modulus and the shear modulus.

Over the past decades, many techniques have been developed to image tissue structures.[4-5,6,7,8,9] Computer Tomography (CT)[10] takes 360 degree X-ray pictures and reconstructs 3D tissue structures using computer software. Magnetic Resonance Imaging (MRI)[11] uses powerful magnetic fields and radio waves to create tissue images for diagnosis. Ultrasound (US)[12] transmits high-frequency waves through tissue and captures the echoes to image tissue structures. T-scan (TS)[13] measures low-level bioelectric currents to produce real-time images of electrical impedance properties of tissues. Ultrasound elastography (UE)[14] evaluates the echo time through tissues under a constant mechanical stress and compares it to that of the same tissue when unstressed. A tissue strain map is then obtained, from which an image of 2D elastic modulus distribution is created by inversion techniques. Tactile imaging tools using array pressure sensors probe spatial tissue stiffness variations. However none of these techniques have the ability to probe tumor interface properties.

The detection of abnormal tissue as cancerous growth requires improvements in screening technologies. The key to successful treatment lies in early detection. Imaging techniques such as mammography in breast cancer screening, detect abnormal tissue by tissue density contrast. Mammography is the only FDA approved breast cancer screening technique, which has a typical sensitivity of 85% that decreases to 65% in radiodense breasts.[10] However, in these screening processes there is a high incidence of false positives. In fact, only about 15-30% of breast biopsies yield a diagnosis of malignancy. Changes in tissue stiffness have increasingly become an important characteristic in disease diagnosis. It is known that breast cancers are calcified tissues that are more than seven times stiffer than normal breast tissues.[11-12,13,14] Thus, contrasting levels of stiffness within the breast may indicate cancerous tissue. Similarly, plaque-lined blood vessels are also stiffer than normal, healthy blood vessels.

The examining physician may detect abnormal tissue stiffness by palpation by taking advantage of the fact that cancerous tissues are stiffer than surrounding normal tissues under compression. Thus, palpation has been a useful tool for experienced physicians to diagnose breast and prostate cancer. However, palpation is not quantitative and depends solely on the experience of the individual physician. So there remains a critical need to improve cancer-screening technology to reduce the number of unnecessary biopsies.

SUMMARY OF THE INVENTION

In a first aspect, the invention relates to a sensor for measuring a compression modulus and a shear modulus that has a first layer made of piezoelectric material, a second layer made of a non-piezoelectric material, a first electrode placed on top of the first layer for sensing a displacement of the first layer; and a second electrode placed on top of the first layer for providing a force to the first layer.

In a second aspect of the invention a sensor for measuring a compression modulus and a shear modulus is provided having a first layer made of piezoelectric material for providing a force, a second layer made of non-piezoelectric material, and a third layer made of piezoelectric material for sensing a displacement.

In a third aspect of the invention a method for measuring a compression modulus and a shear modulus is provided. The method has the steps of providing a plurality of sensors made of a piezoelectric material and a non-piezoelectric material at a target, applying a force with at least one of the plurality of sensors, detecting a displacement with at least one of the plurality of sensors, and providing a measurement of a compression modulus and a shear modulus of said target.

smoothed data, to create an enhanced image, and (d) a representation of the simulated tissue.

Figure 8A:
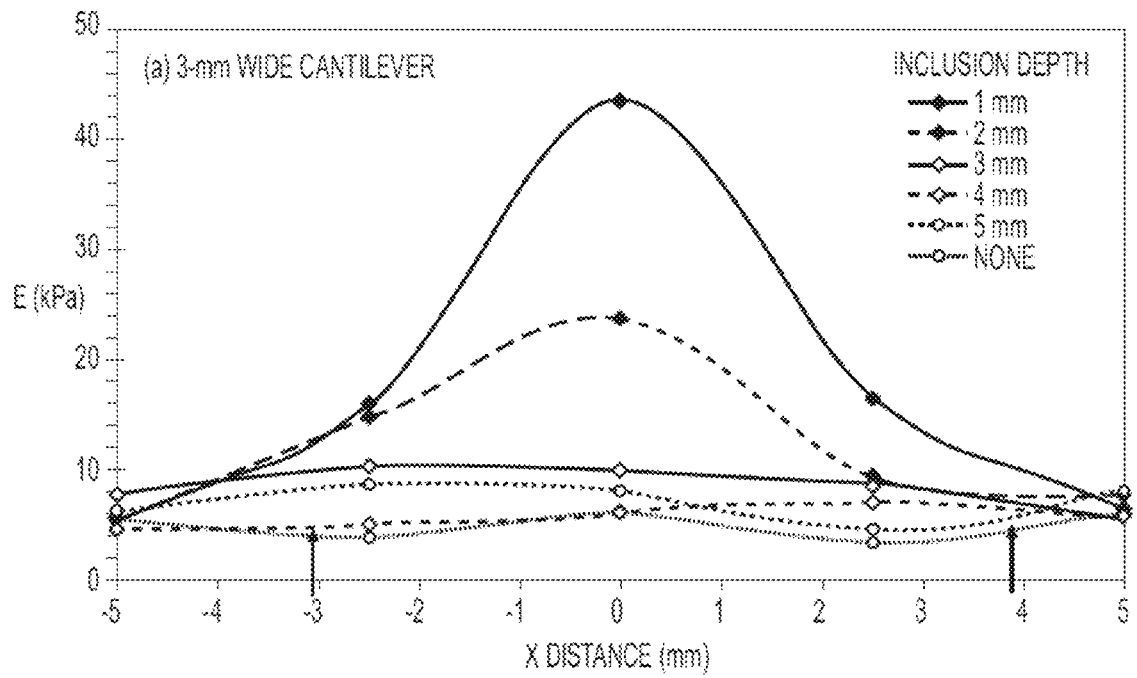

FIG. 8 shows graphs of the elastic modulus profile of (a) 7 mm diameter wax in gelatin at various depth measured with a 3 mm wide cantilever, (b) 15 mm diameter wax in gelatin measured with a 5 mm wide cantilever, and (c) summary of the detection depth limit of 3 mm wide cantilever and 5 mm wide cantilever.

Figure 9:
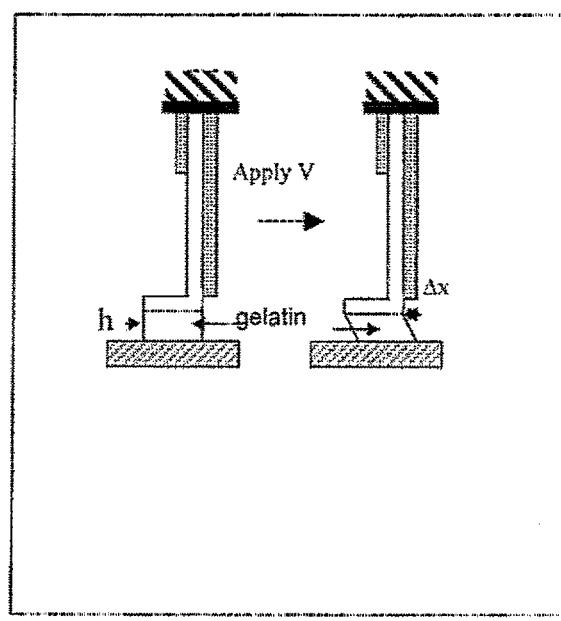

FIG. 9 shows a schematic of a regular shear test using an L-shaped cantilever where the contact area is the same as the sample surface area.

Figure 10:
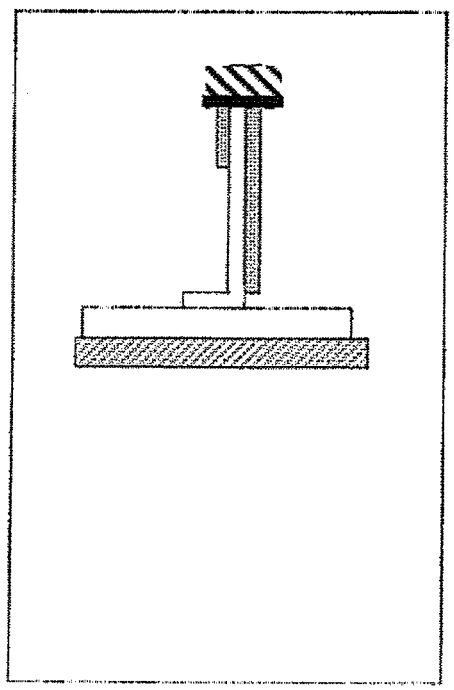

FIG. 10 shows a schematic of an indentation shear test using an L-shaped cantilever where the contact area is much smaller than the sample surface area.

FIGS. 11(a)-11(d) show schematics of regular compression (FIG. 11(a)), indentation compression (FIG. 11(b)), regular shear (FIG. 11(c)), and indentation shear (FIG. 11(d)) measurements using a cantilever that has a U-shaped stainless steel tip. FIG. 11(e) shows an embodiment of a cantilever according to the present invention.

Figure 11:
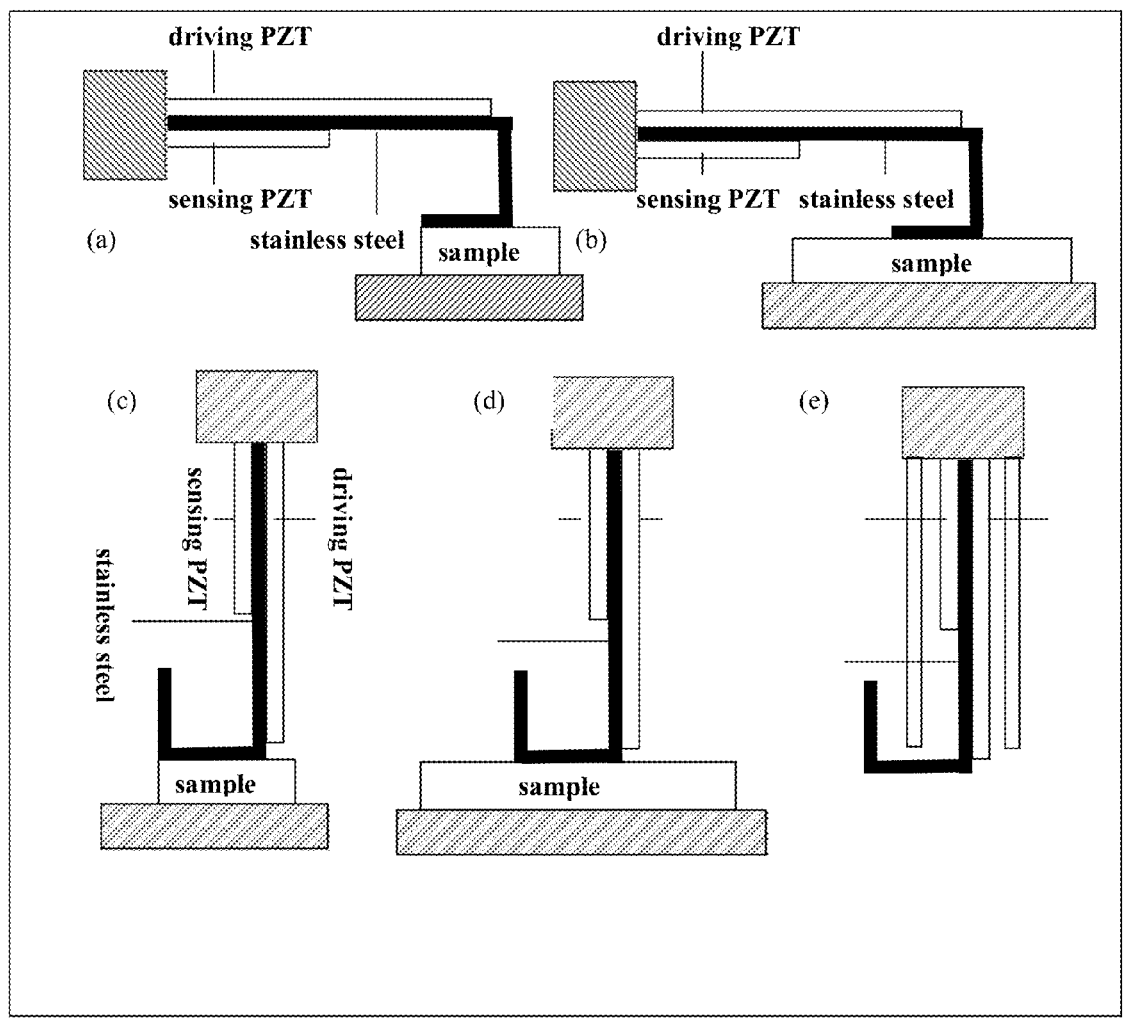
Figure 12:
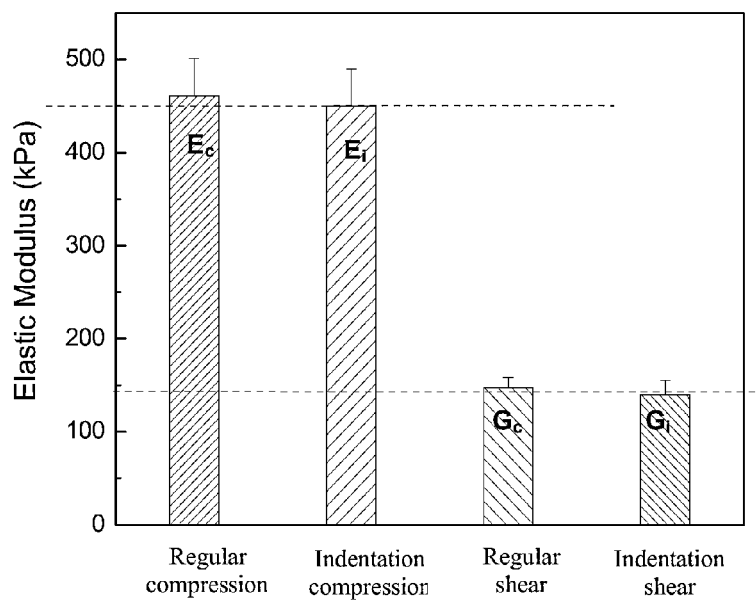

FIG. 12 shows a graph of the results of regular compression, indentation compression, regular shear, and indentation shear measurements on rubber samples that had a young's modulus 400–500 kPa using the U-shaped cantilever as shown in FIG. 11.

Figure 13:
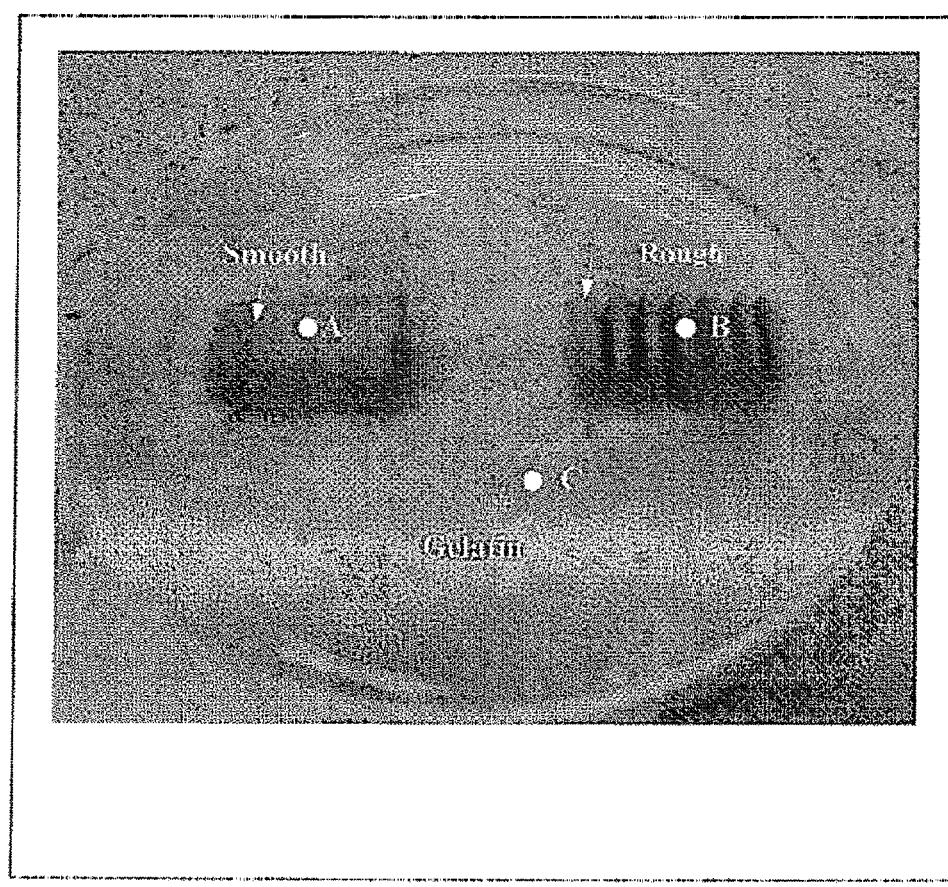

FIG. 13 shows a representation of model tumors and surrounding tissue.

Figure 14:
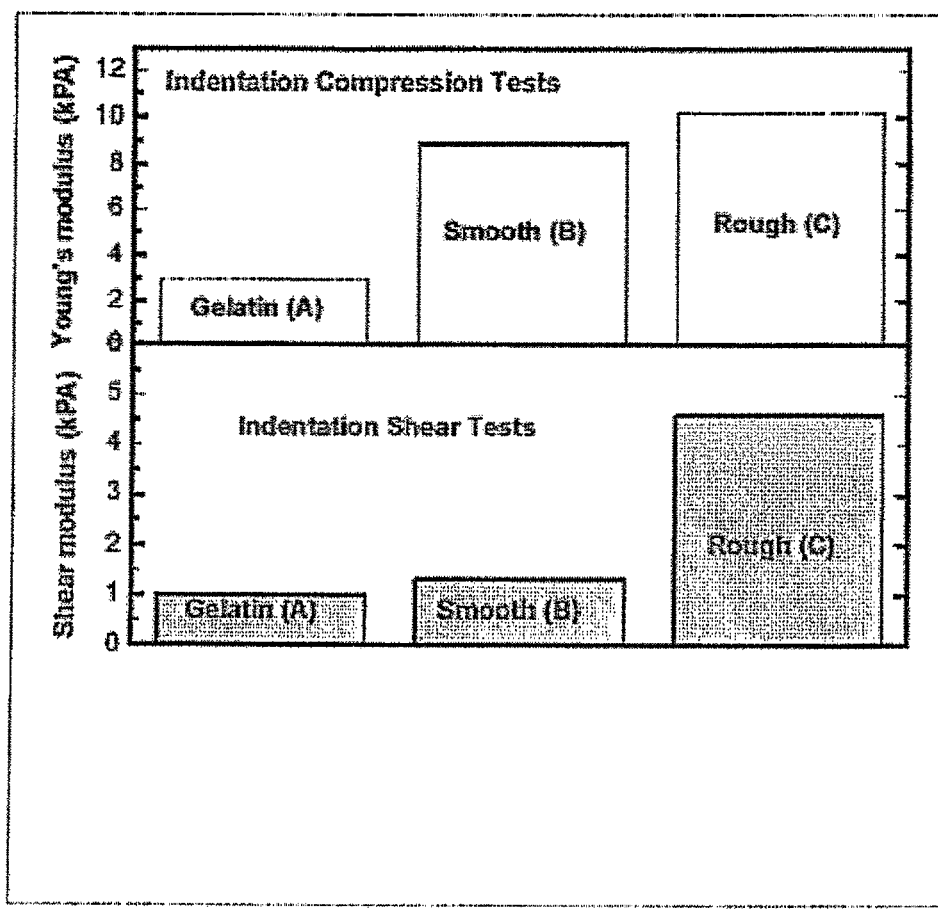

FIG. 14 shows a graphical representation of Young's modulus and shear modulus tests measured by indentation compression and indentation shear tests on various materials.

Figure 15:
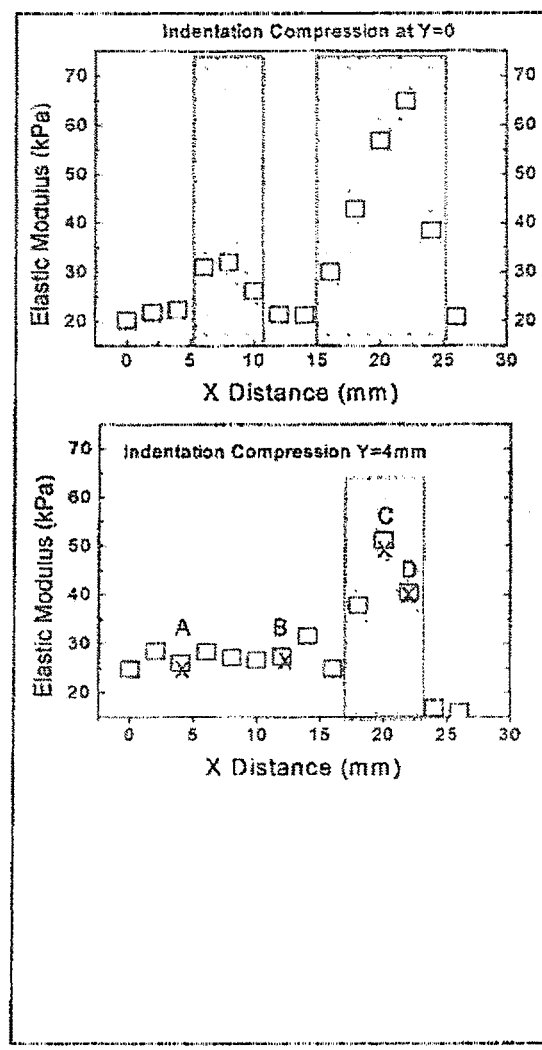

FIG. 15 shows a graph of a lateral elastic modulus profile of a lumpectomy sample.

Figure 16:
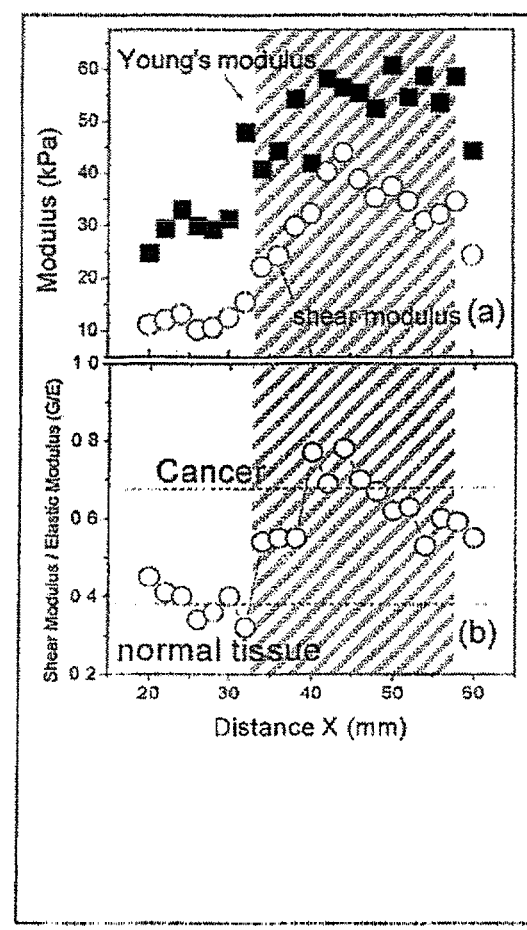

FIG. 16 shows (a) a graph of Young's modulus (E) and shear modulus (G) profiles, and (b) G/E profile on breast tissue with cancer.

Figure 17A:
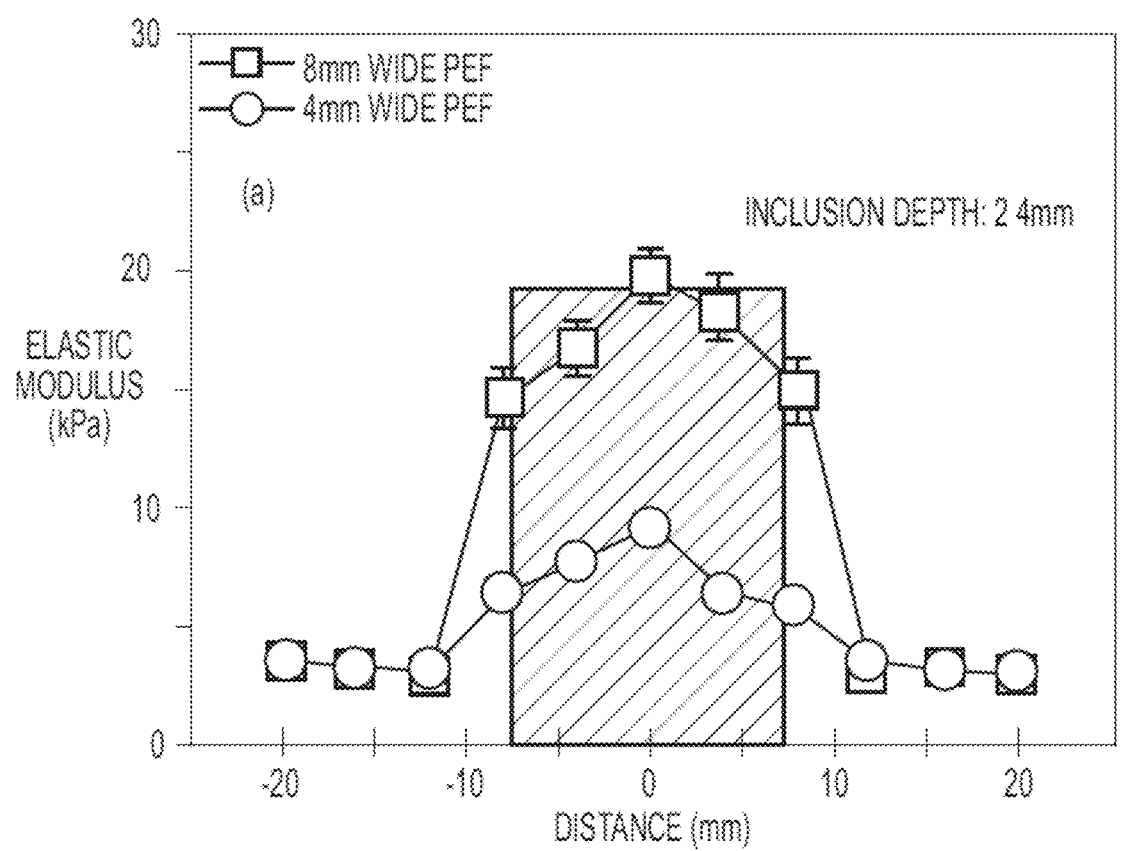
Figure 17B:
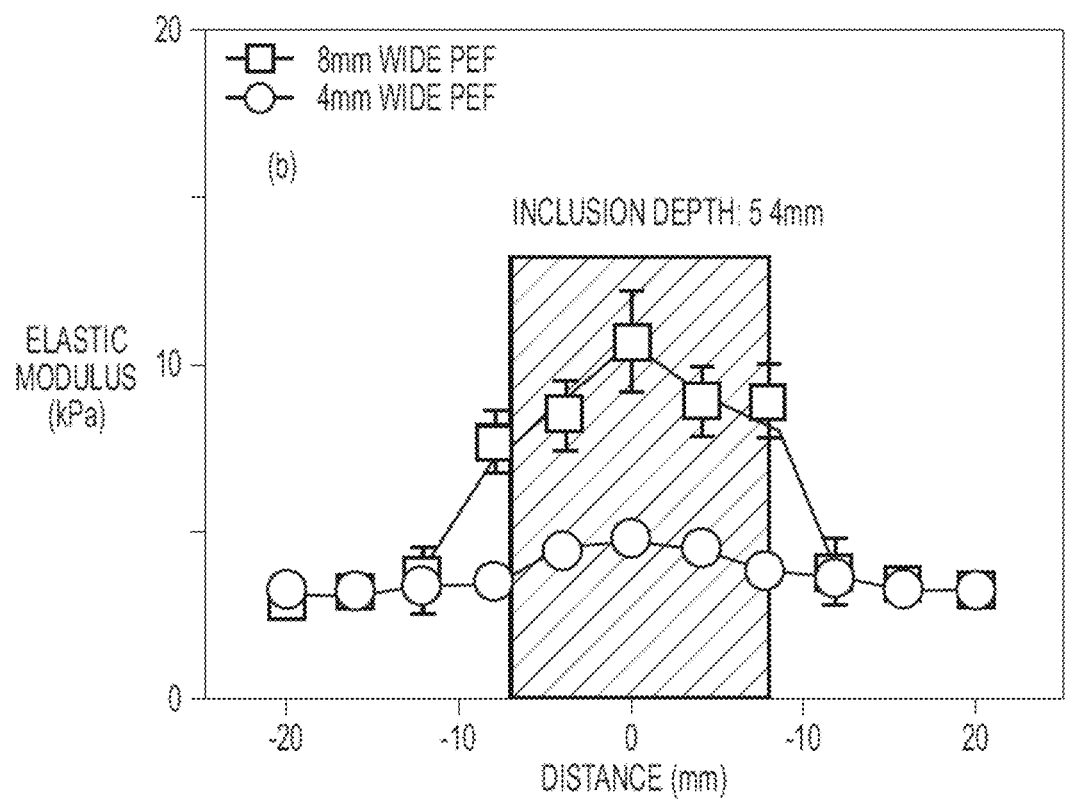

FIG. 17 shows a graph of elastic modulus, E, profiles measured using an 8 mm wide PEF (open squares) and a 4 mm wide PEF (open squares) on a 15 mm diameter clay inclusion in gelatin.

Figure 18:
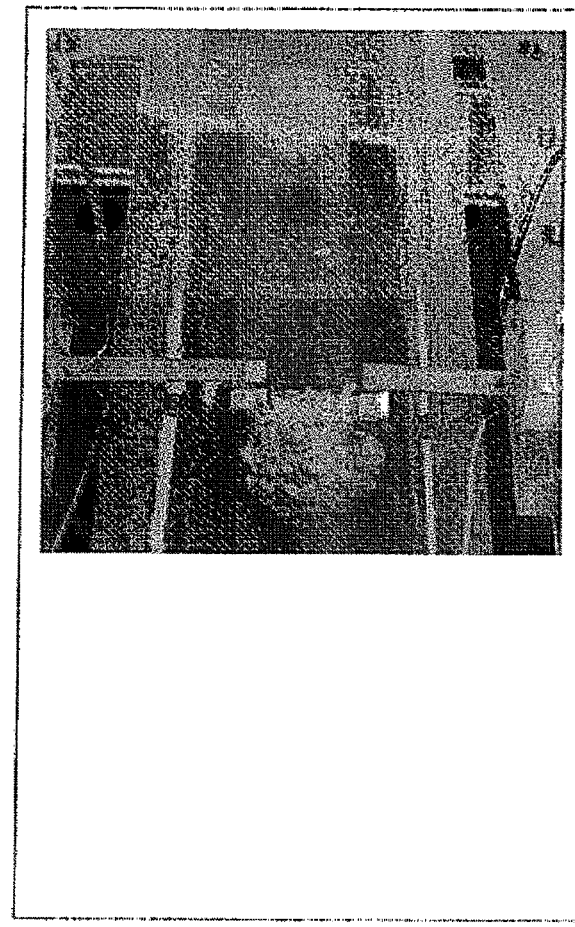

FIG. 18 shows a representation of a direct tumor mobility measurement made on a model rough inclusion (front) and on a model smooth inclusion (back) in gelatin using two PEFs.

DETAILED DESCRIPTION OF THE PREFERRED EMBODIMENT(S)

Figure 1:
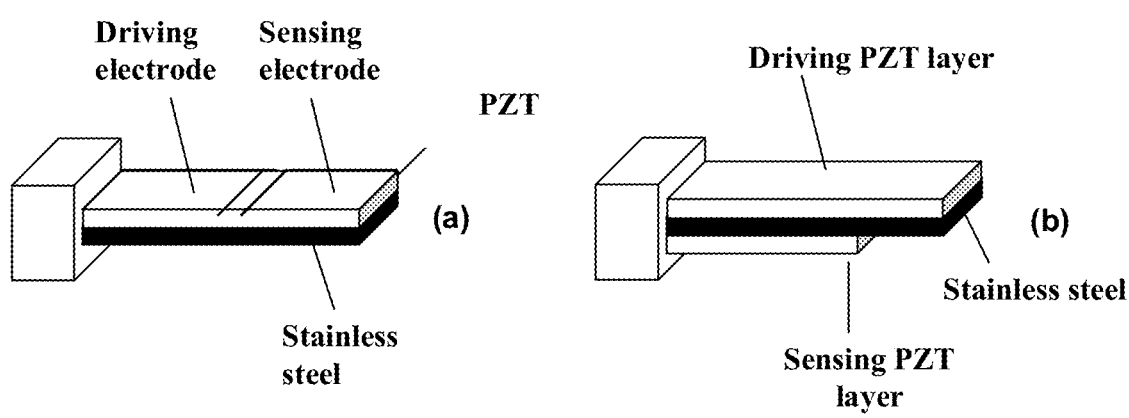
FIG. 1 shows a schematic of two PZT/stainless steel cantilevers with (a) driving and sensing electrodes both on the top side and (b) with a bottom sensing PZT layer.

A "PEFS" includes a piezoelectric layer bonded to a non-piezoelectric layer to form a cantilever. FIG. 1a shows a schematic of a lead zirconate titanate (PZT)/stainless steel cantilever with both the driving and sensing electrodes on the top side. FIG. 1b shows a PZT/stainless steel cantilever with a bottom PZT sensing layer. In these schematics, the PZT represents the piezoelectric layer and the stainless steel represents the non-piezoelectric layer.

In a first aspect of the invention, the PEFS is capable of simultaneously applying a force and detecting the corresponding displacement. The application of a voltage at the driving electrode generates the force and the corresponding displacement is measured by detecting the induced piezoelectric voltage within the sensing electrode. The PEFS can measure both the compressive Young's modulus and the shear modulus of a soft material through the cantilevered tip. Thus, in an aspect of the current invention, the PEFS measures both the compressive Young's modulus and shear modulus using one single device, while at the same time increasing the sensitivity and accuracy of the measurements, relative to some commercially available devices used for this purpose. Comparisons between the shear and compressive measurements using one single device provide clear and accurate information about the interfaces between hard inclusions (tumors) and the surrounding tissue that otherwise could likely not be obtained.

In another aspect of the invention, several PEFS can form an array to measure lateral and in-depth stiffness variations in soft-materials and tissues both under compression and under shear. This ability to self-excite via the driving voltage and self-detect via the sensing electrode allows a PEFS to measure the elastic and shear properties of specimens having complex shapes.

In another aspect of the invention, the PEFS may apply forces and measure displacements at the same time, allowing the device to function using completely electrical means for tissue-stiffness imaging, cancer and disease detection. Thus, the PEFS may be powered with a DC power source allowing the PEFS to take electrical measurements in the DC mode. In this aspect of the invention the PEFS may be part of a portable hand-held device for measuring tissue. This simple all-electrical measurement makes the PEFS look and work like a finger, which may allow for in vivo measurements in tight spaces.

While the sensitivity of the PEFS has been improved by the increased sensitivity of the compression tests with the addition of the shear test to the PEFS, the reduction of the probe size as compared to the bulkiness of current tactile cancer-imaging devices, provides increased versatility as well. In particular, the finger-like shape of the PEFS is now suitable for, for example, prostate cancer detection.

In another aspect of the invention, the PEFS can analyze measurements of various widths allowing the direct experimental determination of a stiffness variation in the thickness direction. Current tumor imaging techniques are incapable of directly measuring a tumor size or position. Instead, these techniques measure the surface mechanical response. The tumor information is generated numerically by the "inversion" technique and used to reconstruct the tumor size and position.[15,16]

In another aspect of the invention, the PEFS can assess vertical stiffness variations of soft materials/tissues up to several centimeters in depth with increased resolution by use of an array of PEFS's of varying probe widths ranging from less than 1 mm to several cm. Detection of tissue stiffness both under shear and under compression will allow comparison of the stiffness of a hard inclusion such as a tumor, with the stiffness of surrounding normal tissue, not only under compression, but also under shear. Such comparisons will permit a determination of the interfacial properties between the hard inclusion and surrounding tissue, which has the potential to greatly enhance the ability to assess tumor malignancy.

The PEFS is capable of detecting soft-material/stiffness variations in both the shear and the compression modes while under DC power. This allows a portable hand held device to detect soft material/tissue stiffness. Additional advantages result from the ultra-small strains employed for detection (smaller than 1%), and the minimal discomfort that such strains will cause to the patient.

In another aspect of the invention, the PEFS may be fabricated in a variety of shapes including L-shaped, U-L-shaped, U-shaped, square-shaped, O-shaped, tapered, etc. as well as in various lengths and widths. When the PEFS has an L-shaped tip, the PEFS is capable of accurately measuring the shear modulus of soft tissues and materials at very small strain (<0.1%), a capability most of the current commercial rheological instruments lack.

In addition to detection and mapping of a tumor, the PEFS may also be employed as a tissue/soft-material mechanical tester, for breast cancer detection, for prostate cancer detection, for monitoring skin cancer and skin elasticity testing, or for cellular elasticity/plasticity measurements using a miniaturized PEFS. Of course, the PEFS is capable of use in conventional methods for making compression and shear measurements on pliable materials of any kind and its use need not be limited to tissue measurements.

All-electrical measurement. When a voltage is applied to the top PZT layer of a PEFS as shown in FIG. 1(b), it causes the PEFS to bend due to the converse piezoelectric effect, which generates a force, and therefore, a displacement at the cantilever tip. The bending of the cantilever generates an induced piezoelectric voltage in the bottom sensing PZT layer, which is in proportion to the displacement at the cantilever tip. By carefully monitoring the displacement at the cantilever tip during a given test, an accurate determination of both the force and displacement exerted on the sample surface can be ascertained, which in turn yields an accurate determination of the elastic modulus of the sample. Moreover, by placing a sensing PZT layer in the device, as shown, the maximum of the induced voltage transient of the sensing PZT can be used to accurately determine the cantilever tip displacement.

The ability of the PEFS to electrically apply a force and electronically measure the displacement makes it ideal for "electronic palpation" like an "electronic finger." The PEFS measures the tissue compressive (shear) stiffness by touching (rubbing) the tissue surface. The force generation and displacement sensing are all within the "finger." The PEFS may be used for in-vivo tissue imaging particularly for breast cancer and prostate cancer detection.

The PEFS can measure elastic stiffness and shear modulus of soft materials, with or without a sensing electrode. In case a sensing electrode is not used, other means such as a laser or piezoelectric displacement meter can be provided for displacement determination.

EXAMPLE 1

Figure 2A:
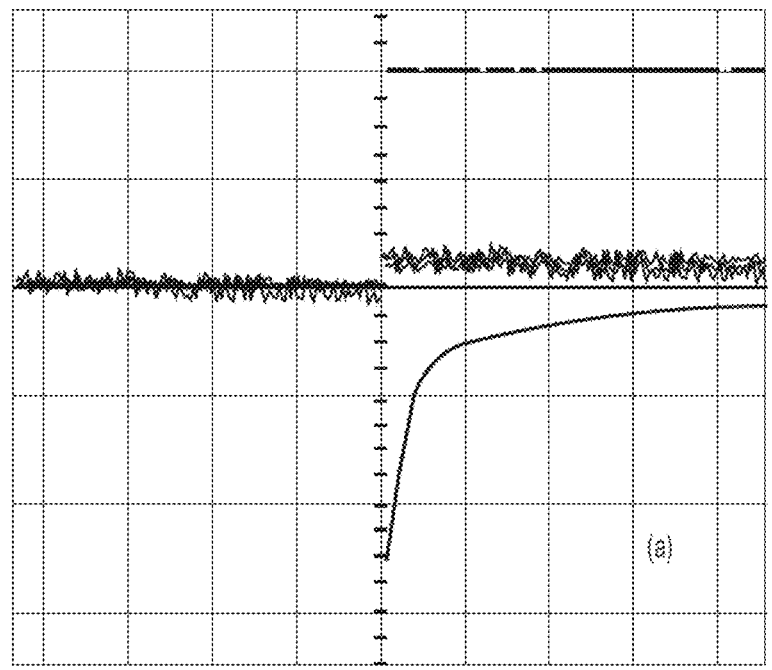
FIG. 2 shows a graph of (a) the displacement signals captured by the sensing PZT layer, and (b) the deflection signal captured by the sensing PZT layer.

FIG. 2(a) shows the displacement signal captured by the sensing PZT layer and by the laser displacement meter when a 10V step potential was applied to the unimorph cantilever. FIG. 2(a) shows a typical all-electrical measurement as displayed on an oscilloscope. The applied voltage (line 1), at t=0, indicates the applied voltage was turned on. Line 2 was the voltage output from the laser displacement meter for direct displacement measurements and line 3 was the induced voltage measured at the sensing PZT layer. In FIG. 2(a) the induced voltage was negative. The peak of the induced voltage was therefore at minimum near t=0. The induced voltage decayed with time due to the fact that the PZT layer was not perfectly insulating. The charge generated at the PZT surface by the cantilever bending dissipated over time. As can be seen from FIG. 2(a), the induced-voltage measurement was more sensitive than that generated by the Commercial displacement meter (Keynce™ LC2450 displacemeter (Line 1)) used.

Figure 2B:
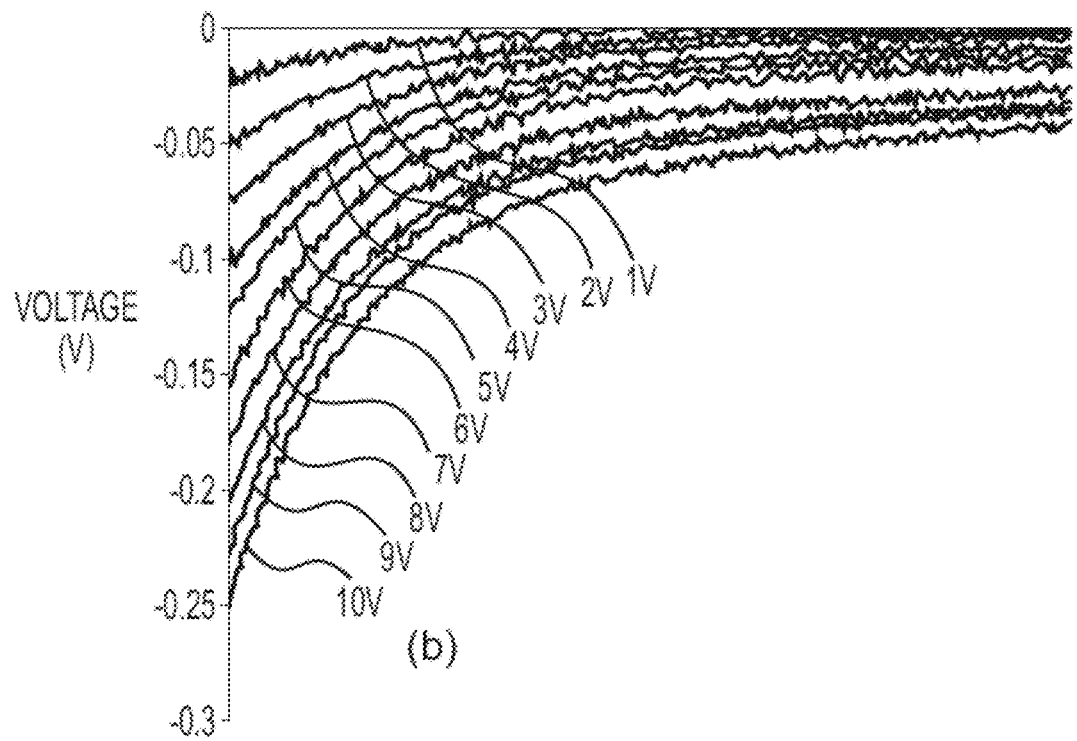

FIG. 2(b) shows the deflection signal captured by the sensing PZT layer at various applied voltages. FIG. 2(b) shows that the induced voltage increased with the applied voltage.

Figure 3:
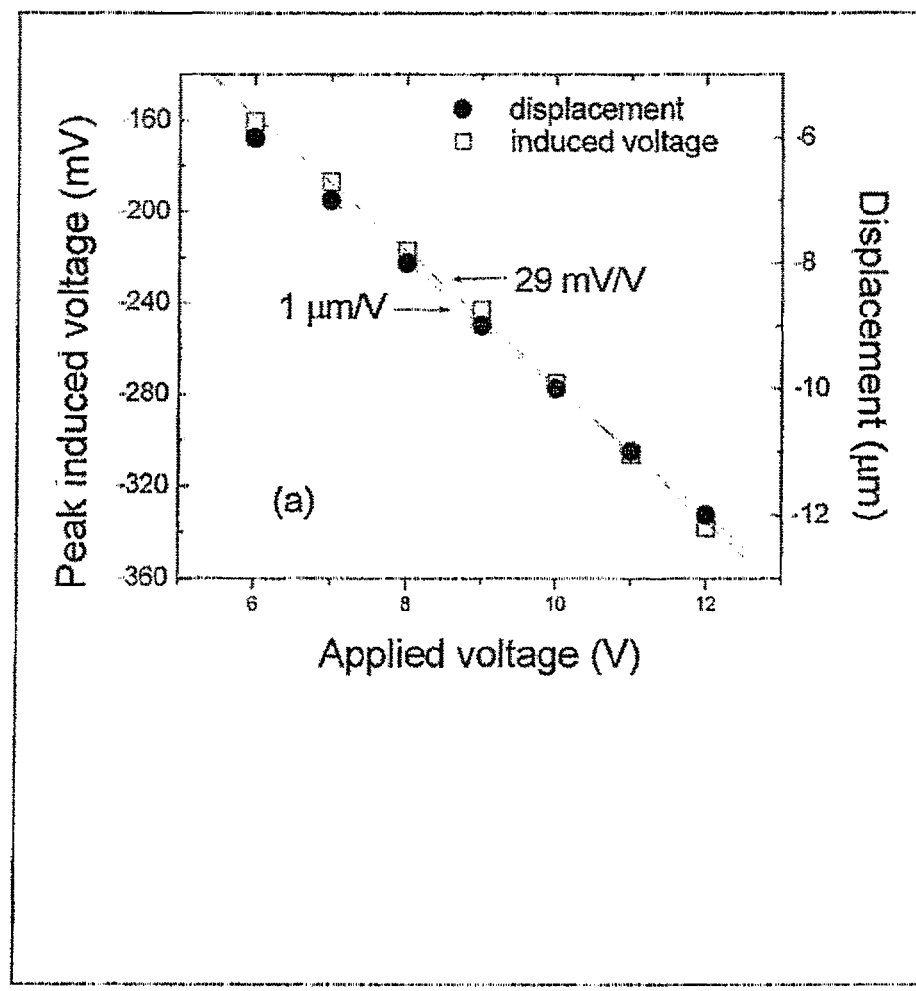
FIG. 3 shows a graph of peak and displacement measurements.

In FIG. 3, the peak induced piezoelectric voltage captured at the sensing electrode (open squares) and the displacement measured by a laser displacement meter (full circles), versus applied voltage, is shown. As can be seen, the peak induced voltage and the displacement are proportional to each other, validating that the displacement at the tip of the cantilever can be quantified using the peak induced voltage measured at the bottom sensing PZT layer.

EXAMPLE 2

Flat-Punch Indentation Compression Test

A flat-punch indentation compression test is a test whereby the cantilever tip is pressed on the sample surface and the cantilever contact area is much smaller than the sample surface area. This test simulates an in vivo measurement.

Figure 4:
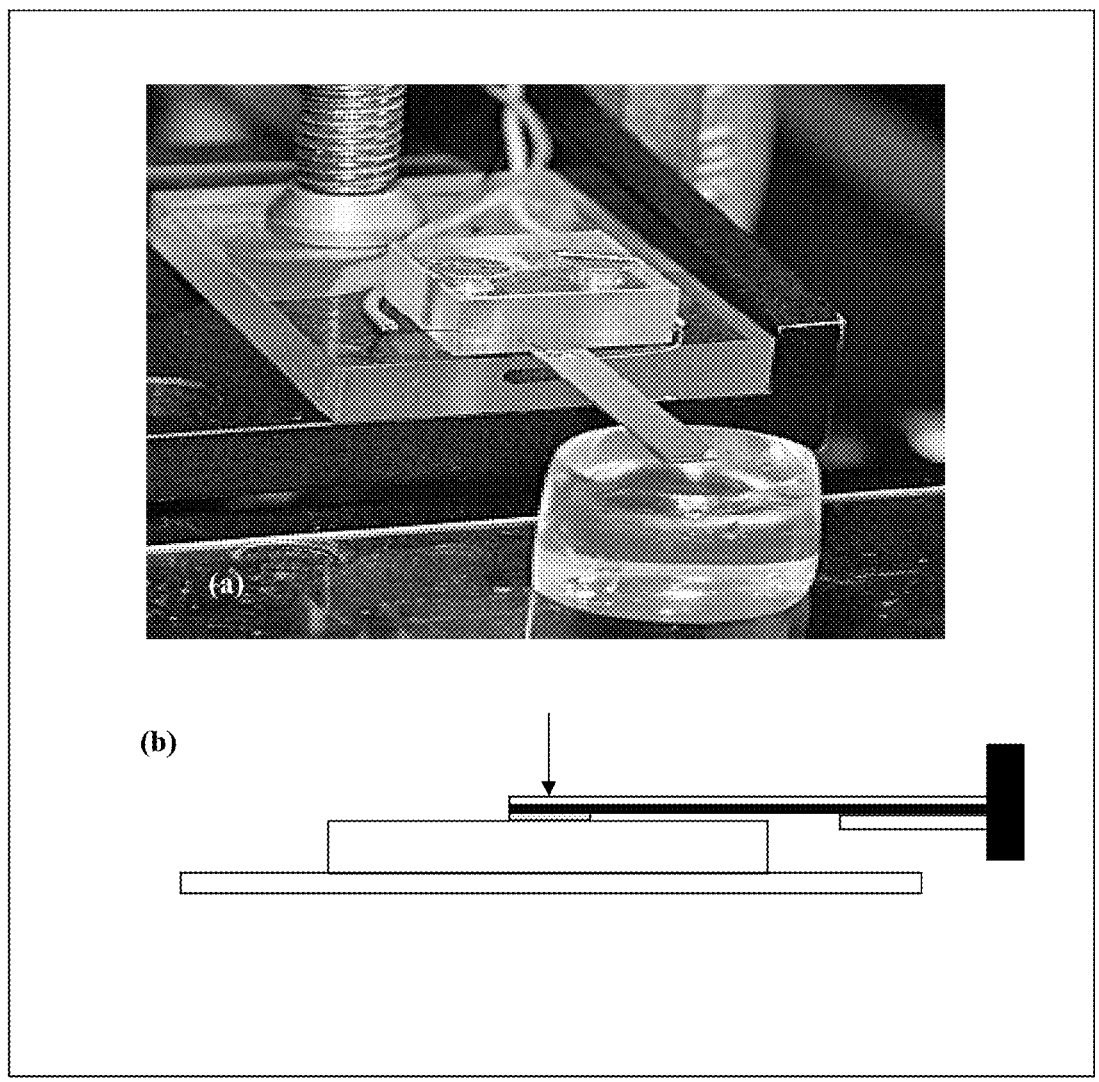
FIG. 4 shows a representation and schematic of the compression indentation tests.

FIG. 4(a) is a representation of an indentation compression test on a model soft tissue using a PEFS with a sensing PZT layer, and FIG. 4(b) is a schematic of the compression indentation test. In the flat-punch indentation compression tests, the contact area, A, which was much smaller than the sample surface, was defined by gluing a thin plastic sheet of a known area on the underside of the cantilever as schematically shown in the setup depicted in FIG. 4(b). Using a traditional Hertzian indentation analysis one can relate load, displacement, contact area, and the mechanical properties of the tested material.[17] When applying a voltage to the top, driving PZT layer, it generated a force, F, and caused indentation displacement, $\delta$ to the sample. The relationship between the force, F, and the displacement, $\delta$, is described by the following expression.

$$F = 2\sqrt{\frac{A}{\pi}} \frac{E}{1-v^2} \delta, \tag{1}$$

wherein $v$ is the Poisson ratio and E is the Young's modulus of the model tissue. Denoting the spring constant of the cantilever as K and the "free" displacement generated by an applied voltage V is represented as $d_0$, the force F exerted on the model tissue by the applied voltage V with a displacement, $\delta$, is therefore, $F=K(d_0-\delta)$. It follows that the Young's modulus, E, is then expressed as, $$E_i = \frac{\sqrt{\pi}}{2}(1-v^2)\frac{K(d_0-\delta)}{\delta\sqrt{A}}, \tag{2}$$

wherein the subscript i of E denotes indentation.

EXAMPLE 3

Regular Compression Test

Figure 5:
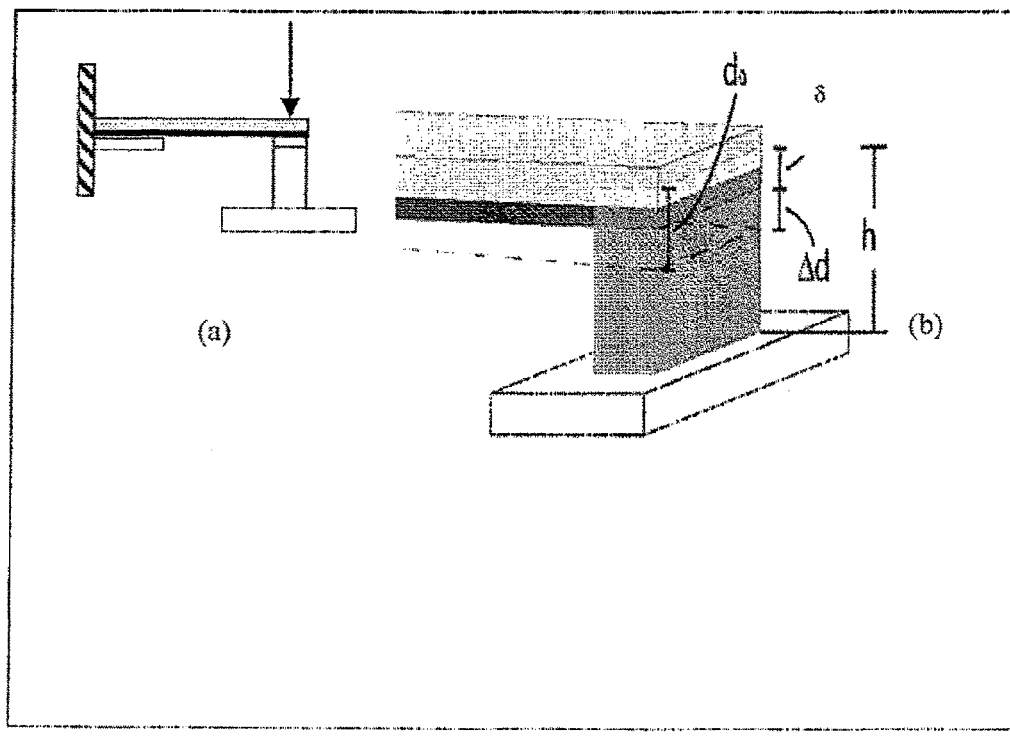
FIG. 5 shows (a) a regular compression test where the contact area is the same as the surface area, and (b) deformation of a sample in a regular compression test under an applied voltage, V.
Figure 6:
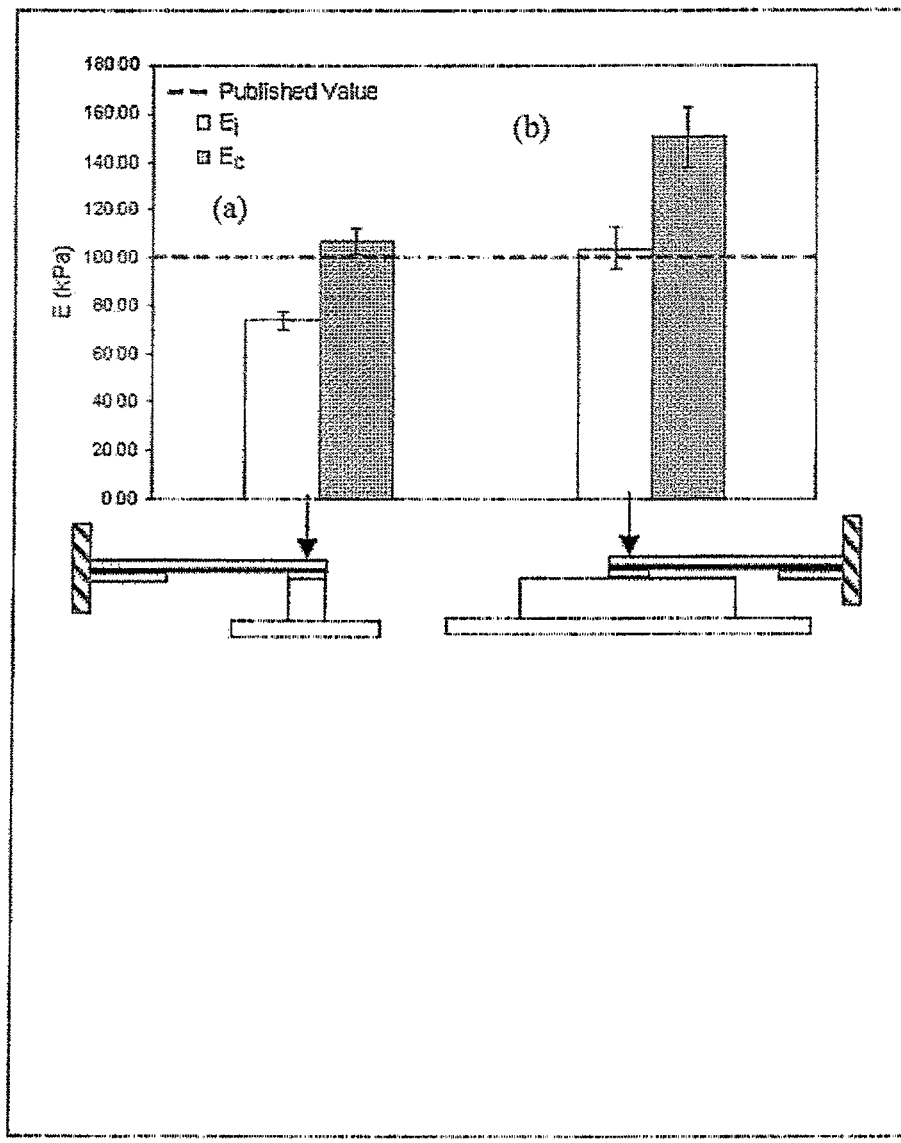
FIG. 6 shows a comparison of the elastic modulus obtained in a regular compression test and an indentation compression test.

A regular compression test describes a condition where a cantilever is pressed on the sample surface and the contact area is the same as the sample surface area. A schematic of a regular compression test is shown in FIG. 5(a) where the contact area is the same as the surface area. FIG. 5(b) is a schematic of the deformation of a sample in a regular compression test under an applied voltage, V. In a regular compression test, the elastic modulus is obtained by using $$E_c = \frac{K(d_0-\delta)h}{A\delta}, \tag{3}$$

wherein h is the height of the sample, $d_0$ the "free" displacement of the cantilever at voltage V, $\delta$ the displacement with the sample, K the spring constant of the cantilever and $E_c$ is the elastic modulus measured by the regular compression test. For comparison, the same model tissue sample was tested using both the indentation compression and regular compression test conditions (the left-hand set of data and setup in FIG. 6(a) for regular compression and the right-hand data and setup for indentation compression in FIG. 6(b)). The elastic moduli, $E_i$ and $E_c$ were obtained using Eq. (2) and Eq. (3), respectively. Clearly, $E_c$ obtained using Eq. (3) under the compression condition and $E_1$ obtained using Eq. (2) under the indentation condition agreed with each other and also with the known value, 100 KPa, of the elastic modulus of the rubber employed for the test, thereby validating the elastic modulus measurements using both the indentation test and the compression test. These results clearly established that the elastic stiffness of tissue can be determined using flat-punch indentation tests with the piezoelectric cantilever of the present invention.

EXAMPLE 4

Tissue-Stiffness Imaging by Indentation Compression

Figure 7A:
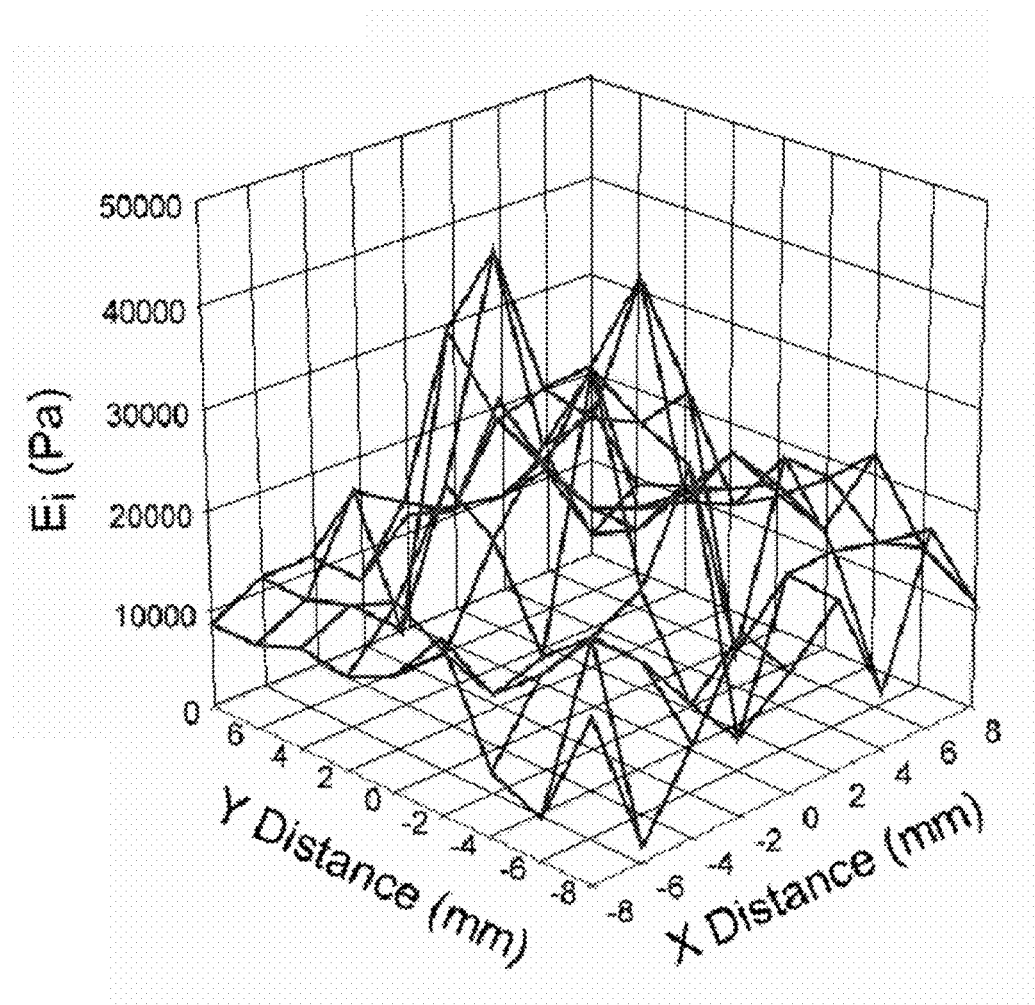
FIG. 7 shows (a) a 3-D plot of raw elastic modulus data from indentation tests, (b) the corresponding contour plot, (c)
Figure 7B:
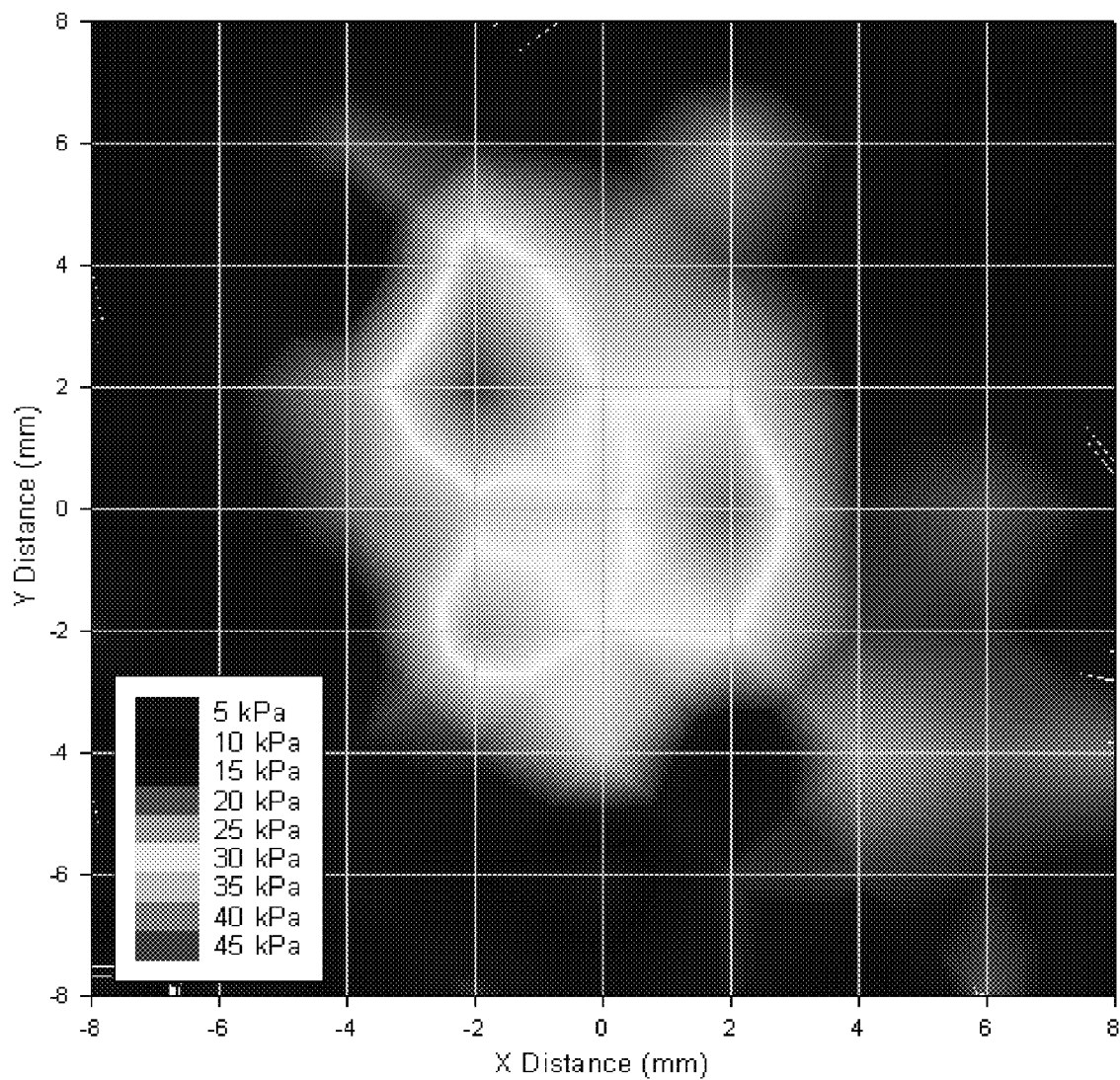
Figure 7C:
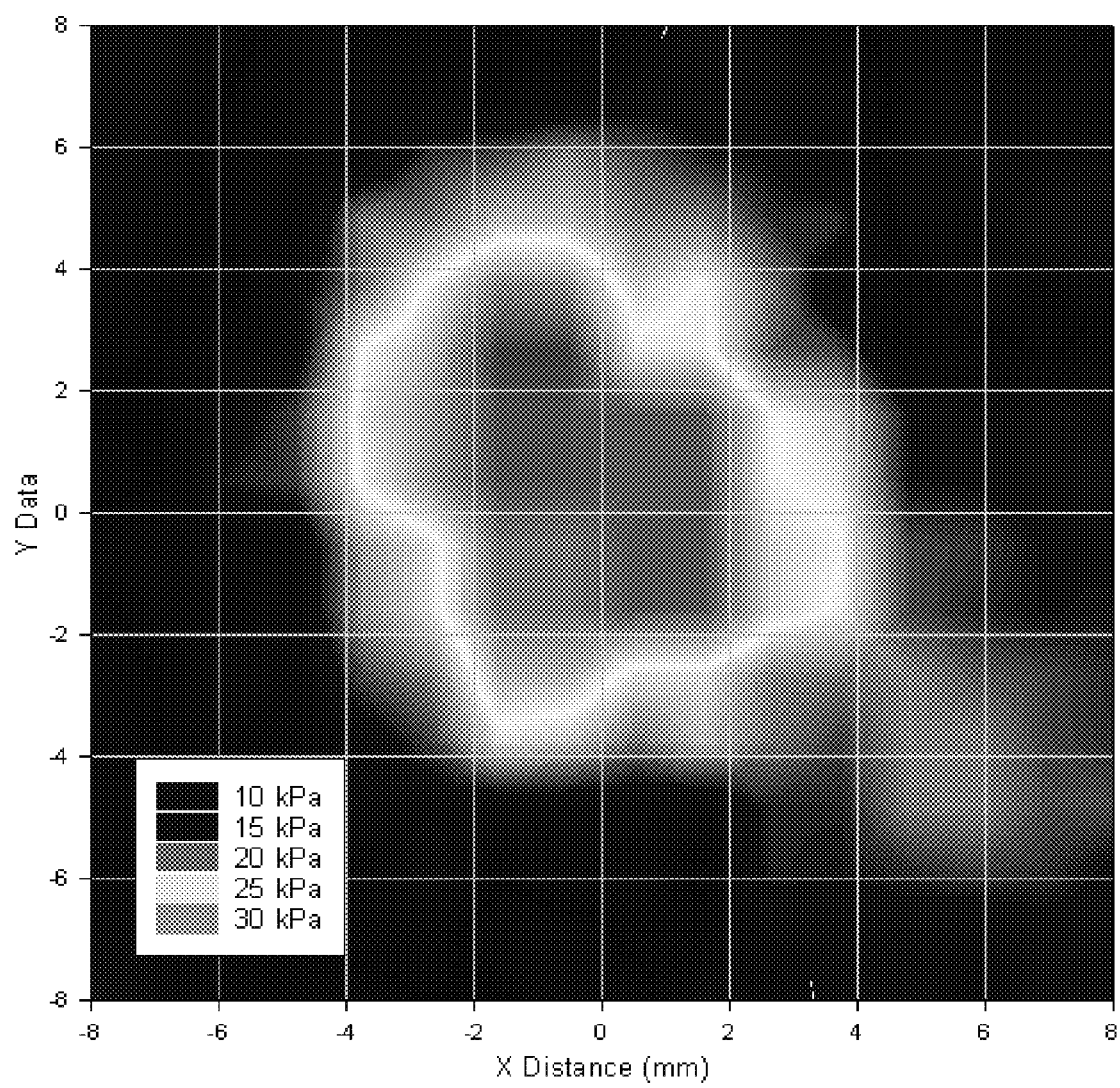
Figure 7D:
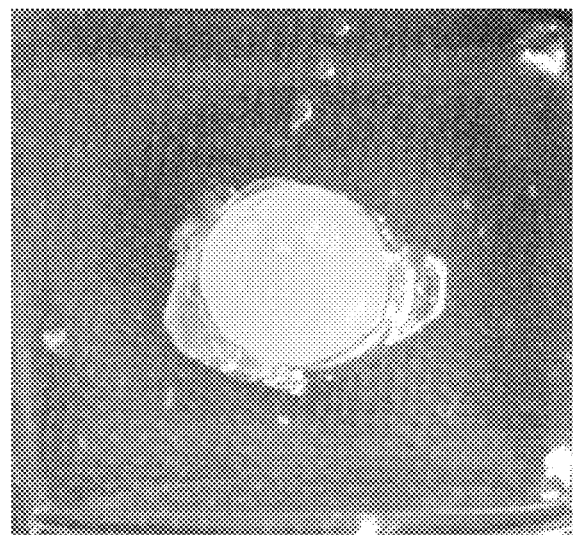

Having demonstrated that piezoelectric cantilevers are capable of determining the elastic stiffness of soft materials using the flat-punch indentation test, and that the test can be done with a driving electrode for force generation, and a sensing electrode for displacement/force detection using all-electrical measurements, here it is demonstrated that tissue elastic stiffness profiling can be done using flat-punch indentation. A simulated tissue sample with a hard inclusion was made from gelatin and candle wax. A 7 mm diameter, 5 mm tall cylinder of wax was embedded in an 8 mm thick gelatin matrix. Indentation tests were conducted at 2 mm increments over the entire surface surrounding the inclusion. The elastic modulus at each location was calculated using Eq. (2). The 2-D plot in FIG. 7(a) reflects the higher modulus values in the center, plainly evident in the corresponding contour plot (FIG. 7(b)). The image was enhanced in FIG. 7(c) through a data smoothing operation, and is seen in comparison with FIG. 7(d) to depict the approximate size and shape of the wax.

EXAMPLE 5

Dependence of Depth Limit in Detection on Probe Size

Because the indentation test only needs to press a small part of the sample surface, it is a natural configuration for in vivo application. However, because the probe size is smaller than the sample size in an indentation test, only the volume immediately beneath the indenting device is affected by the indentation test. It is thus conceivable that the detection sensitivity depends on the depth of the hard inclusion. To demonstrate this point, the effect of the probe size on the depth limit for detection using cantilevers of 3 mm width and 5 mm width was examined. Both cantilevers are 2 cm in length. The 3 mm wide cantilever had a contact area of 3 mm (the width)×2 mm and the 5 mm wide cantilever had a contact area of 5 mm (the width)×2 mm. With the 3 mm wide cantilever six wax inclusions of 7 mm diameters at varying depths beneath the top surface were embedded in a gelatin sample of 7 mm in height. For the 5 mm wide cantilever, five wax inclusions 15 mm in diameter were embedded in a gelatin sample of 18 mm in height. Cantilever indentation tests were conducted across the central axis of each sample at 1 mm increments. Elastic modulus was calculated at each location using the indentation formula, Equation (2). The result of elastic profiles of wax inclusions 7 mm in diameter embedded at different depths measured using the 3 mm wide cantilever are plotted in FIG. 8(a). Clearly, the 3 mm wide cantilever could detect the variation in the elastic modulus for depths less than 2-3 mm. When the wax inclusion was at a depth larger than 3 mm, there was no difference in the elastic modulus measured by the cantilever.

Figure 8B:
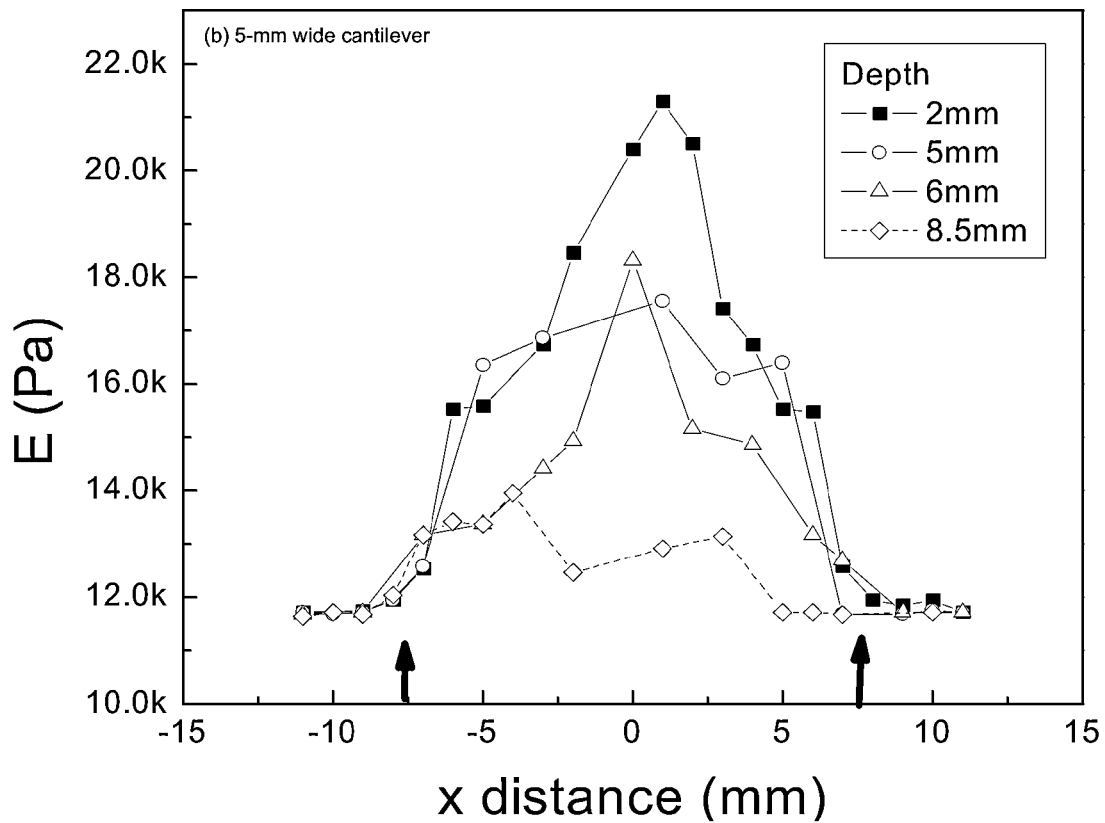
Figure 8C:
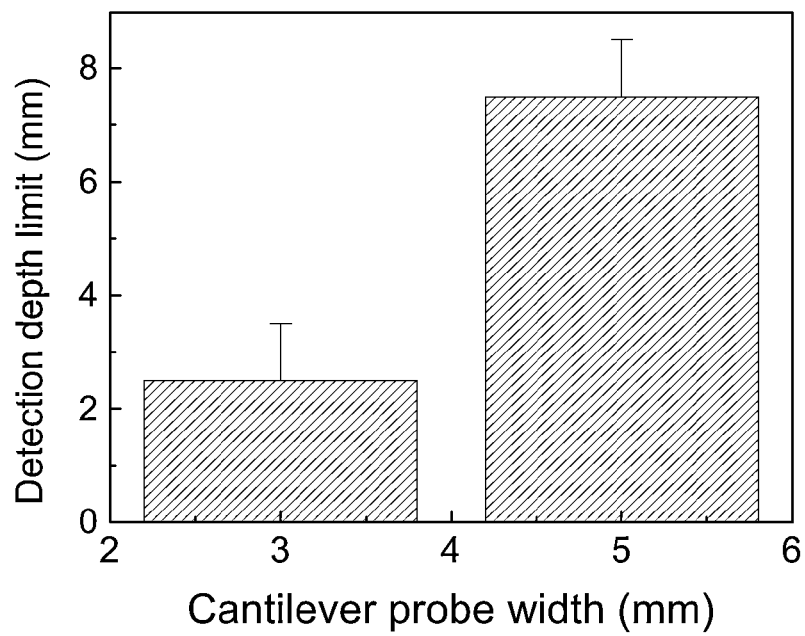

For comparison, the result of elastic profiles of wax inclusions 15 mm in diameter embedded at different depths were measured using the 5 mm wide cantilever and plotted in FIG. 8(b). With a 5 mm wide cantilever, the elastic modulus variation due to the wax inclusion could be detected at a larger depth. From FIG. 8(b), it can be seen that depth limit on the detection by a 5 mm long cantilever was about 8 mm. Comparing the elastic modulus profile results measured from the 3 mm and 5 mm cantilevers, it is clear that a wider cantilever (or wider probe) allowed detection of elastic modulus variation at a greater depth. The effect of the cantilever width on the detection depth limit is shown in FIG. 8(c).

The above results indicate that one can probe the elastic stiffness to different depths by using cantilevers having different probe sizes. Furthermore, by carefully analyzing measurements with different probe sizes, it is possible to obtain not only the stiffness variation in the lateral direction, but also in the thickness direction to thereby allow construction of 3-D tissue stiffness maps.

EXAMPLE 6

Regular Shear Test

Shear tests can be accomplished using L-shaped cantilevers. A schematic of a regular shear test is shown in FIG. 9. When a voltage was applied across the PZT, which is shown as the shaded layer in FIG. 9, it caused the cantilever to bend, which created lateral movement of the L-shaped tip and sheared the tissue sample underneath. The shear modulus can be determined using the equation:

$$G_c = \frac{K(\Delta x_0 - \Delta x)h}{A\Delta x}, \quad (4)$$

where h and A are the height and the surface area of the sample, respectively, K is the spring constant of the cantilever, and $\Delta x_0$ and $\Delta x$ the displacement of the cantilever without and with the sample, respectively.

EXAMPLE 7

Indentation Shear Test

A schematic of an indentation shear test is shown in FIG. 10. This is the most relevant condition for potential tissue shear stiffness measurement. When a voltage was applied across the PZT, it caused the cantilever to bend, which created lateral movement of the L-shaped tip and sheared the tissue sample underneath. The shear modulus can be determined using the equation:

$$G_i = \frac{\sqrt{\pi}}{2}(1-v^2)\frac{K(\Delta x_0 - \Delta x)}{\Delta x\sqrt{A}}, \quad (5)$$

wherein A is the contact area, v is the Poisson ratio, K is the spring constant of the cantilever, and $\Delta x_0$ and $\Delta x$ are the displacements of the cantilever without and with the sample, respectively.

EXAMPLE 8

Comparison of All Four Measurements

For comparison of all four measurements, regular compression, indentation compression, regular shear and indentation shear, a cantilever that has a U-shaped stainless steel tip as shown in FIGS. 11(a)-11(d) was used. The advantages of such U-shaped tips include: (1) precise control of the contact area in all measurement geometry, and (2) the ability to allow the cantilever to be protected during measurements in tight spaces as illustrated by (e). The cantilever had a driving PZT layer 23 mm long, and a sensing PZT layer 10 mm long. The cantilever is 4 mm wide. Both the driving and sensing PZT layers are 127 μm thick and the stainless steel layer is 50 μm thick. The measurements were done on rubber samples with a Young's modulus of 400–500 kPa.

The results of the regular compression, indentation compression, regular shear, and indentation shear measurements on rubber samples that had a Young's modulus of 400–500 kPa using the U-shaped cantilever as shown in FIGS. 11(a)-11(e), are summarized in FIG. 12. The Young's modulus obtained from regular compression with Eq. (3) and the shear modulus obtained from regular shear measurements with Eq. (4) were 460 kPa and 148 kPa, respectively, giving a Poisson ratio of 0.5, consistent with what was expected of rubber samples. Using a Poisson ratio of 0.5, the Young's modulus and shear modulus obtained from indentation measurements with Eqs. (2) and (5) were 452 kPa and 141 kPa, respectively, in close agreement with the values obtained from the regular compression and regular shear measurements. The results shown in FIG. 12 validate the measurement of the Young's modulus using either the regular compression test or the indentation compression test, and validate the measurements of the shear modulus using either the regular shear test or indentation shear test.

EXAMPLE 9

Distinguishing Tumor Interfacial Properties by Indentation Shear Tests

Two tumor models, one with a smooth face and the other with a rough face were made of play dough and were the same size and embedded at the same depth in the model tissue gelatin as shown in FIG. 13. Both the smooth-surfaced tumor and the rough-surfaced tumor were 2 mm beneath the gelatin surface. Indentation compression and indentation shear tests were carried out on the plain gelatin surface (point A), and on the gelatin surface above the center of the smooth-surfaced tumor (point B), and above the center of the rough-surfaced tumor (point C). FIG. 14 shows the Young's modulus and shear modulus measured on plain gelatin (point A), the smooth-surfaced model tumor (B), and the rough-surfaced tumor (C) using the indentation compression and the indentation shear tests.

While both the smooth-surfaced and rough-surfaced model tumors were much stiffer than the surrounding gelatin under compression, only the rough-surfaced tumor displayed a stiffer shear. This indicates that the rough-surfaced tumor model was less mobile than the smooth-surfaced tumor model under shear. Thus, the indentation shear measurement with a piezoelectric finger was effective in probing tumor interfacial properties and tumor mobility. Combining both the compression and shear tests offers the potential of not only measuring the stiffness, but also determining the mobility of a tumor, which has great potential for tumor malignancy detection.

EXAMPLE 10

Detecting Small Satellite Tumor Missed in Preoperative Screening

The use of the PEFS in excised breast tumors has been evaluated in the laboratory. The lumpectomy specimen was from a 60-year old woman with breast cancer. The known malignancy was 1.4 cm in the largest dimension. After surgical excision, the specimen was oriented with silk sutures, scanned with ultrasound, and images were stored. The PEFS scan was performed in the same orientation to allow later correlation with the ultrasound image. The specimen was sectioned in the same orientation to allow histological confirmation of the PEFS findings as well. Using the PEFS, preliminary elastic modulus measurements were performed on breast lumpectomy samples using an 8 mm wide PEFS with a rectangular tip. FIG. 15 shows lateral elastic modulus profile of a lumpectomy sample measured by an 8 mm wide PEFS at (a) along y=0 which exhibited two tumors, a larger one at x=17-25 mm, and a smaller one at x=5-10, and at (b) along y=4 mm, which only exhibited the larger tumor at x=17-25. The dotted rectangles are meant to guide the eye. The PEFS could distinguish the cancers from the surrounding tissues.

Of note, the PEFS scan identified the known 15×13×12 mm invasive ductal carcinoma at x=15-25 mm and identified a smaller 6×5×3 mm satellite invasive ductal carcinoma at x=5-10 mm. This smaller lesion was not detected by mammogram, ultrasound or the physician's preoperative palpation.

EXAMPLE 11

Comparison of Shear Modulus to Elastic Modulus Profile of Breast Cancer

With the second lumpectomy sample (not shown), the elastic modulus, E, and shear modulus, G, profiles have been performed. The tumor was 12-10 mm in size and 5 mm below the surface. The tissue was examined with an 8 mm wide PEFS. FIG. 16 shows (a) Young's modulus (E) and shear modulus (G) profiles, and (b) G/E profile on breast tissue with cancer. The resultant elastic modulus and shear modulus profiles are shown in FIG. 16(a). Clearly both the elastic modulus and the shear modulus were much higher in the region with the tumor than in the surrounding tissue. The G/E profile is plotted in FIG. 16(b). The G/E ratio was much higher (approaching 0.6-0.7) in the tumor region than that of the surrounding tissues (around 0.3-0.4). The G/E ratio of 0.3 in the normal tissue region was expected of an isotropic material with a Poisson's ratio of 0.5.[2] A much higher G/E ratio in the cancer region indicated that the tumor was harder to move under shear than under compression as compared to the surrounding normal tissue. The pathological session result confirmed the malignancy.

EXAMPLE 12

Simultaneous Determination of Depth and Elastic Modulus of Tumors Using Two PEFS's of Different Widths In FIG. 17 parts (a) and (b), are shown the lateral elastic modulus profiles of a 15 mm diameter model clay tumor in gelatin with 2.4 mm (part (a)), and 5.4 mm (part (b)) depths, as respectively measured by a 4 mm wide (the open squares) and an 8 mm wide PEFS (the open squares). The lateral location of the clay was marked by the gray shaded rectangle. Comparing the profiles obtained with 8 mm wide PEFS and those obtained by the 4 mm wide PEFS, one can see that far away from the inclusion, the values of the elastic modulus of the gelatin obtained by both PEFS's were essentially the same, indicating no inclusion underneath. Proximate to the inclusion, the values of the measured elastic moduli differed between the two PEFS' as they had different probe depths.

A separate experiment (not shown) has determined that the probe depth of a PEFS is twice the PEFS's width. With $E_{gel}$ obtained from locations far away from the inclusion, one can then use the two profiles measured with the two PEFS' to solve the following two equations for the two unknowns, $E_{inclusion}$ and d:

$$\frac{d_{p,1}}{E_{measured,1}} = \frac{d}{E_{gel}} + \frac{d_{p,1} - d}{E_{inclusion}}, \text{ and} \quad (6)$$

$$\frac{d_{p,2}}{E_{measured,1}} = \frac{d}{E_{gel}} + \frac{d_{p,2} - d}{E_{inclusion}}, \quad (7)$$

where $d_{p,1}$ and $d_{p,2}$ ($E_{measured,1}$ and $E_{measured,2}$) are the probe depths of PEFS 1 and PEFS 2, respectively, $E_{gel}$ the elastic modulus of gelatin that can be obtained from far away from the inclusion, and d and $E_{inclusion}$ are the inclusion depth and the elastic modulus of the inclusion. Using the measured elastic modulus over the top of the center of the inclusion, the known probe depths, and the $E_{gel}$ obtained from far away from the inclusion and solving Eqs. (6) and (7), we obtained d=2.4 mm and $E_{inclusion}$=109 kPa from FIG. 17 part (a) and d=5.4 mm and $E_{inclusion}$=102 kPa from FIG. 17 part (b). Both the deduced inclusion depths and $E_{inclusion}$ are in agreement with the independently measured values: 2.4 mm, 5.4 mm, and 104 kPa, respectively. This clearly illustrates that lateral elastic modulus profiles measured with two PEFS' of different widths can be used to directly deduce both the inclusion depth and the inclusion elastic modulus. With more PEFS', it should be possible to obtain even more detailed axial elastic modulus profile information.

EXAMPLE 13

Direct Tumor Mobility Measurement Using Two PEFS'

In this model study, a model smooth tumor (the shaded inclusion in the back of FIG. 18) and a model rough (malignant) tumor (the white rough ball in the front of FIG. 18) were prepared. Direct tumor mobility measurement was carried out with one PEFS pushing on the side of the tumor and the other PEFS determining the movement of the tumor on the other side. With the driving PEFS pushing down 50 μm, a movement of 2 mm from the smooth inclusion and no movement from the rough inclusion were measured. This illustrated the sensitivity of the PEFS to directly measure tumor mobility for potential malignancy screening.

Preliminary measurement on breast tissues after surgery have indicated that a PEFS can detect cancerous tumors as small as 3 mm in size that were missed by mammography, ultrasound, and physician's palpation, offering great potential for early breast cancer detection. Furthermore, it was demonstrated that by using two or more PEFS's of different widths, one can simultaneously determine both the tumor elastic (shear) modulus and its depth. In addition, it has also been demonstrated that tumor mobility can be assessed by measuring the ratio of the shear modulus to the elastic modulus of a tumor, or by sensitive direct tumor mobility measurement using two PEFS's, one for pushing and one for measuring the movement. The tumor mobility measurement offers the potential for non-invasive breast cancer malignancy screening.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

The below list of references is incorporated herein in their entirety.

[1] Wellman, R. D. Howe, E. Dalton, K. A. Kern, "Breast Tissue Stiffness in Compression is Correlated to Histological Diagnosis," http://biorobotics.harvard.edu/pubs/mech-props.pdf.

[2] http://www.zfm.ethz.ch/e/res/bio/#Overview.

[3] http://www.tainst.com/products/rheology.html

[4] R. Ferrini, E. Mannino, E. Ramsdell, and L. Hill, "Screening Mammography for Breast Cancer: American College of Preventive Medicine Practice Policy Statement," http://www.acpm.org/breast.htm.

[5] A Keller, R Gunderson, O Reikeras, J I Brox, "Reliability of Computed Tomography Measurements of Paraspinal Muscle Cross-sectional Area and Density in Patients with Chronic Low Back Pain," *SPINE* 28 (13): 1455-1460, JULY 1 (2003).

[6] V. Straub, K. M. Donahue, V. Allamand, R. L. Davisson, Y. R. Kim, and K. P. Campbell, "Contrast Agent-Enhanced Magnetic Resonance Imaging of Skeletal Muscle Damage in Animal Models of Muscular Dystrophy," *Magnetic resonance in medicine* 44:655-659 (2000).

[7] L. Gao, K. J. Parker, R. M. Lerner and S. F. Levinson, "Imaging of the elastic properties of tissue-A review," *Ultrasound in Med. & Biol.*, 22[8], 959-77 (1996).

[8] O. Kwon, "T-scan Electrical Impedance Imaging system for anomaly detection." http://parter.kaist.ac.kr/imi/data/Tscan.doc.

[9] S. G. Garlier, C. L. de Kotre, E. Brusseau, J. A. Schaar. P. W. Serruys, and A. F. W. van der Steen, "Elastography," *Journal of Cardiovascular Risk*, 9: 237-245 (2002).

[10] E. D. Rosenberg, W. C. Hunt, and M. R. Williamson, *Radiology* 209, 511 (1998).

[11] S. A Kruse, J. A. Smith, A. J. Lawrence, M. A. Dresner, A. Manduca, J. F. Greenleaf, and R. L. Ehman, "Tissue Characterization using Magnetic Resonance Elastography: Preliminary Results," *Phys. Med. Biol.*, 45 1579-1590 (2000)

[12] L. S. Wilson, D. E. Robinson, and M. J. Dadd, "Elastography—the Movement Begins," *Phys. Med. Biol.*, 45 1409-1421 (2000)

[13] Wellman, P. S, Dalton, E. P., Krag, D., Kern, K. A., Howe, R. D. "Tactile Imaging of Breast Masses First Clinical Report," *Archives of Surgery* 136(2), 204-08 (2001)

[14] J. F. Greenleaf, M. Fatemi, M. Insana, "Selected Methods for Imaging Elastic Properties of Biological Tissues," *Annu. Rev. Biomed. Eng.* 5, 57-78 (2003)

[15] P. S. Wellman, R. D. Howe, N. Dewagan, M. A. Cundari, E. Dalton, and K. A. Kern, "Tactile Imaging: A Method For Documenting Breast Lumps," http://biorobotics.harvard.edu/pubs/tactile.pdf.

[16] Y. Wang, C. Nguyen, R. Srikanchana, Z. Geng, M. T. Freedman, "Tactile Mapping of Palpable Abnormalities for Breast Cancer Diagnosis," http://www.imac.georgetown.edu/members/resumes/.. %5CWebServer%20Documents%5CD oc_P_22_F.pdf.

The invention claimed is:

1. A sensor system comprising:
a cantilever including:
a first piezoelectric layer, wherein a portion of said piezoelectric layer forms an exposed contact surface for contacting a sample and a second piezoelectric layer electrically separated from the first piezoelectric layer;
an apparatus for generating a force in said cantilever; and
a means for measuring a displacement of said piezoelectric layer resultant from said generated force and wherein said sensor is capable of simultaneously inducing a force in said cantilever and measuring a displacement of one said piezoelectric layer.

2. The sensor system of claim 1, wherein the means for measuring a displacement of said piezoelectric layer comprises an apparatus for measuring a voltage, wherein the measured voltage is indicative of the displacement.

3. The sensor system of claim 1, wherein the means for measuring a displacement of said piezoelectric layer is selected from the group consisting of: a laser and a piezoelectric displacement meter.

4. The sensor system of claim 1, wherein said second piezoelectric layer comprises a portion that extends beyond the other piezoelectric layer and wherein said portion has a shape selected from the group consisting of: a substantially square-shaped configuration, a substantially L-shaped configuration, a substantially U-shaped configuration, a substantially O-shaped configuration and a tapered configuration.

5. The sensor system of claim 1, wherein said second piezoelectric layer comprises a portion that extends beyond said first piezoelectric layer and wherein said portion is oriented at an angle greater than or less than 180 degrees with respect to said first piezoelectric layer.

6. The sensor system of claim 5, wherein said portion is oriented at about a 90 degree angle with respect to a remainder of said second piezoelectric layer.

7. The sensor system of claim 1, comprising two or more of said cantilevers, and wherein at least two of said cantilevers have different dimensions.

8. The sensor system of claim 7, wherein the at least two cantilevers have different widths.

9. A sensor system comprising:
a cantilever including:
a first piezoelectric layer enabled to provide a force;
a second piezoelectric layer;
an apparatus for applying a voltage to said first piezoelectric layer to generate a force in said cantilever;
a means for measuring a displacement of said second piezoelectric layer resultant from said generated force and wherein a portion of a surface of at least one said piezoelectric layer forms an exposed surface portion for contacting a sample.

10. A sensor system as claimed in claim 9, wherein said piezoelectric layers are the same length.

11. A sensor as claimed in claim 9, wherein said first and second piezoelectric layers are electrically isolated from one another.

12. A method for determining a compression modulus of a substrate comprising the steps of;
applying a compressive force to the substrate via a sensor having a cantilever including a piezoelectric material, when said sensor is in contact with a substrate comprising a target;
detecting a displacement of the cantilever due to said compressive force;
determining a compression modulus of said substrate from said detected displacement.

13. The method of claim 12, further comprising the step of determining a depth of a target located within the substrate.

14. The method of claim 12, wherein the step of determining the compression modulus comprises determining the compression modulus at a plurality of different depths within the substrate.

15. The method of claim 12, wherein said target is a tumor or tissue surrounding a tumor.

16. A method for determining a shear modulus of a substrate comprising the steps of;
applying a shear force to said substrate via a sensor having a cantilever including a piezoelectric material when said sensor is in contact with the substrate;
detecting a displacement of the cantilever due to said shear force; and
determining a shear modulus of said substrate from said detected displacement.

17. The method of claim 16, wherein said substrate is a tumor or tissue surrounding a tumor.

18. The method of claim 17, wherein a plurality of said sensors are employed in said method in an array and further comprising at least one step selected from the group consisting of: mapping a tumor, determining tumor stiffness and determining tumor mobility.

* * * * *